(12) United States Patent
Wanaski et al.

(10) Patent No.: US 11,083,737 B1
(45) Date of Patent: Aug. 10, 2021

(54) METHODS OF ADMINISTERING DEFLAZACORT THERAPY

(71) Applicant: PTC Therapeutics, Inc., South Plainfield, NJ (US)

(72) Inventors: Stephen P. Wanaski, Chicago, IL (US); Virginia D. Schmith, Durham, NC (US); Linda L. Grasfeder, Durham, NC (US); Scott Joseph Brantley, Durham, NC (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 114 days.

(21) Appl. No.: 15/607,130

(22) Filed: May 26, 2017

Related U.S. Application Data

(60) Provisional application No. 62/408,482, filed on Oct. 14, 2016, provisional application No. 62/342,628, filed on May 27, 2016.

(51) Int. Cl.
| | |
|---|---|
| *A61K 31/58* | (2006.01) |
| *A61K 45/06* | (2006.01) |
| *A61K 9/00* | (2006.01) |
| *A61K 9/10* | (2006.01) |
| *A61K 9/20* | (2006.01) |
| *G06F 19/00* | (2018.01) |
| *A61J 1/05* | (2006.01) |
| *A61B 5/00* | (2006.01) |
| *A61B 5/22* | (2006.01) |
| *A61B 5/08* | (2006.01) |

(52) U.S. Cl.
CPC ............. *A61K 31/58* (2013.01); *A61B 5/08* (2013.01); *A61B 5/224* (2013.01); *A61B 5/4848* (2013.01); *A61J 1/05* (2013.01); *A61K 9/0053* (2013.01); *A61K 9/10* (2013.01); *A61K 9/20* (2013.01); *A61K 45/06* (2013.01); *G06F 19/3456* (2013.01)

(58) Field of Classification Search
CPC ............ A61K 31/58; A61K 9/20; A61K 9/10; A61K 9/0053; A61K 45/06; A61B 5/08; A61B 5/224; A61B 5/4848; A61J 1/05
USPC ........................................................ 514/171
See application file for complete search history.

(56) References Cited

U.S. PATENT DOCUMENTS

2019/0054113 A1* 2/2019 Kaye .................... A61K 9/0019

OTHER PUBLICATIONS

Bonifati et al., "A Multicenter, Double-Blind, Randomized Trial of Deflazacort Versus Prednisone in Duchenne Muscular Dystrophy", 2000, Muscle & Nerve, 13(9), pp. 1344-1347. (Year: 2000).*
Biggar et al., "Deflazacort in Duchenne muscular dystrophy: a comparison of two different protocols", 2004, Neuromuscular Disorders, 14(8-9), pp. 476-482. (Year: 2004).*
Houde et al., "Deflazacort Use in Duchenne Muscular Dystrophy: An 8-Year Follow-Up", 2008, Pediatric Neurology, vol. 38, No. 3, pp. 200-206. (Year: 2008).*
Bushby et al., "Diagnosis and management of Duchenne muscular dystrophy, part 1: diagnosis, and pharmacological and psychosocial management", 2010, Lancet Neurol., 9(1), pp. 77-93. (Year: 2010).*
Moxley et al., "Change in Natural History of Duchenne Muscular Dystrophy With Long-term Corticosteroid Treatment: Implications for Management", 2010, Journal of Child Neurology, 25(9), pp. 1116-1129. (Year: 2010).*
Hoffman et al., "Novel Approaches to Corticosteroid Treatment in Duchenne Muscular Dystrophy", 2012, Phys Med Rehabil Clin N Am., 23(4), pp. 821-828. (Year: 2012).*
Griggs et al., "Corticosteroids in Duchenne Muscular Dystrophy: Major Variations in Practice", 2013, Muscle & Nerve, 48(1), pp. 27-31. (Year: 2013).*
Dooley et al., "The Impact of Deflazacort on Puberty in Duchenne Muscular Dystrophy", 2013, Pediatric Neurology, 49(4), pp. 292-293. (Year: 2013).*
Pereira et al., "Co-administration of deflazacort and doxycycline: a potential pharmacotherapy for Duchenne muscular dystrophy", 2015, Clinical and Experimental Pharmacology and Physiology, 42(7), pp. 788-794. (Year: 2015).*
Gloss et al., "Practice guideline update summary:Corticosteroid treatment of Duchenne muscular dystrophy", 2016, Neurology, 86(5), pp. 465-472. (Year: 2016).*
Bushby et al., "Collaborating to bring new therapies to the patient—the TREAT-NMD model", 2009, Acta Myologica, 28(1), pp. 12-15. (Year: 2009).*
Astellas Pharma (2015). "MYRBETRIQ-mirabegron tablet, film coated, extended release Prescribing Information". Downloaded from the Internet at: <https://dailymed.nlm.nih.gov/dailymed/fda/fdaDrugXsl.cfm?setid=ba9e9e15-e666-4c56-9271-2e24739cfa2d&type=display>. (Labeled dose was assessed in a Phase 2 study, referred to as Study 3 in the package insert).
Bello et al., Prednisone/prednisolone and deflazacort regimens in the CINRG Duchenne Natural History Study, Neurology, 85(12):1048-55 (2015).
Bushby et al., Diagnosis and management of Duchenne muscular dystrophy, part 2: implementation of multidisciplinary care, Lancet Neurol., 9(2):177-89 (2010).
Ciafaloni et al., Delayed diagnosis in duchenne muscular dystrophy: data from the Muscular Dystrophy Surveillance, Tracking, and Research Network (MD STARnet), J. Pediatr., 155(3):380-5 (2009).
Eagle et al., Survival in Duchenne muscular dystrophy: improvements in life expectancy since 1967 and the impact of home nocturnal ventilation, Neuromuscul. Disord., 12(10:926-9 (2002).

(Continued)

*Primary Examiner* — My-Chau T. Tran
(74) *Attorney, Agent, or Firm* — Marshall, Gerstein & Borun LLP

(57) ABSTRACT

The disclosure provides a deflazacort therapy comprising, administering to a subject suffering from Duchenne muscular dystrophy (DMD) a fixed dose of deflazacort. Also provided is a deflazacort therapy comprising, increasing the deflazacort dosage when the subject loses ambulation; or, increasing the dosage of deflazacort administered during concomitant administration of a CYP3A4 inducer; or, decreasing the dosage of deflazacort administered during concomitant administration of a CYP3A inhibitor.

13 Claims, 14 Drawing Sheets

(56) References Cited

OTHER PUBLICATIONS

Huang et al., The utility of modeling and simulation in drug development and regulatory review, J. Pharm. Sci., 102(9):2912-23 (2013).

Humbertclaude et al., Motor and respiratory heterogeneity in Duchenne patients: implication for clinical trials, Eur. J. Paediatr. Neurol., 16(2):149-60 (2012).

Koenig et al., Complete cloning of the Duchenne muscular dystrophy (DMD) cDNA and preliminary genomic organization of the DMD gene in normal and affected individuals, Cell, 50(3):509-17 (1987).

Lee et al., Impact of pharmacometric analyses on new drug approval and labelling decisions: a review of 198 submissions between 2000 and 2008, Clin. Pharmacokinet., 50(10:627-35 (2011).

Manzur et al., Glucocorticoid corticosteroids for Duchenne muscular dystrophy, Cochrane Database Syst. Rev., (1):CD003725 (2008).

Mendell et al., Evidence-based path to newborn screening for Duchenne muscular dystrophy, Ann. Neurol., 71(3):304-13 (2012).

Yu et al., Utility of Exposure-Response Analysis in Regulatory Decision on the Selection of Starting Dose of Pasireotide for Cushing Disease, J. Clin. Pharmacol., 56(8):1035-8 (2016).

* cited by examiner

Figure 17

|  | Efficacy | | | AEs | |
|---|---|---|---|---|---|
|  | 12 Week Change in Muscle Strength (mean±SD)[a] | 52 Week Change in Muscle Strength (mean±SD)[a] | 52 Wk FVC Responder Rate | 52 Wk Proportion of Subjects with Weight Gain | 52 Wk Proportion of Subjects with Cushingoid AEs |
| Study 001 Simulated Distribution, 0.9 mg/kg/day DFZ[a] | 0.185±0.250 | 0.424±0.445 | 0.626 | 0.286 | 0.600 |
| Study 001 Simulated Distribution, 1.2 mg/kg/day DFZ[a] | 0.310±0.384 | 0.369±0.545 | 0.636 | 0.328 | 0.687 |
| Placebo | -0.072±0.058 | -- | -- | -- | -- |
| Prednisone | 0.278±0.052 | 0.212±0.076 | 0.365 | 0.354 | 0.768 |
| 0.9 mg/kg/day DFZ (Current Dosing Table) | 0.214±0.061 | 0.396±0.088 | 0.600 | 0.293 | 0.613 |
| 2 Age Groups (Lower Doses) ≤11y=18 mg, >11y=36 mg | 0.194±0.058 | 0.400±0.085 | 0.592 | 0.284 | 0.594 |
| 2 Age Groups (Higher Doses), ≤11y=24 mg, >11y=42 mg | 0.237±0.059 | 0.392±0.089 | 0.624 | 0.306 | 0.640 |
| 2 Weight Groups (Lower Doses) ≤30kg=18 mg, >30kg=36 mg | 0.201±0.058 | 0.400±0.087 | 0.595 | 0.286 | 0.602 |
| 2 Weight Groups (Higher Doses), ≤30kg=24 mg, >30kg=42 mg | 0.241±0.059 | 0.392±0.088 | 0.624 | 0.307 | 0.643 |
| 3 Weight Groups, ≤30kg=18 mg, >30-≤50kg=36 mg, >50kg=48 mg | 0.205±0.060 | 0.397±0.088 | 0.598 | 0.290 | 0.607 |
| 4 Weight Groups, ≤16kg=12 mg, >16-≤30kg=24 mg, >30-≤50kg=42 mg, >50kg=54 mg | 0.240±0.061 | 0.389±0.088 | 0.621 | 0.306 | 0.637 |
| 54 mg to all subjects | 0.284±0.065 | 0.374±0.095 | 0.633 | 0.322 | 0.674 |

Figure 18

|  | Efficacy | | | AEs | |
| --- | --- | --- | --- | --- | --- |
|  | 12 Week Change in Muscle Strength (mean±SD) | 52 Week Change in Muscle Strength (mean±SD) | 52 Wk FVC Responder Rate | 52 Wk Proportion of Subjects with Weight Gain | 52 Wk Proportion of Subjects with Cushingoid AEs |
| Current DFZ Dosing Table[a] | 0.257±0.067 | 0.373±0.096 | 0.613 | 0.308 | 0.645 |
| Placebo[a] | 0.070±0.057 | -- | -- | -- | -- |
| Prednisone[a] | 0.278±0.055 | 0.205±0.077 | 0.364 | 0.354 | 0.768 |
| 2 Age Groups, Amb&≤11=18, NA&≤11=24, Amb&>11=36, NA&>11=42 | 0.248±0.065 | 0.388±0.096 | 0.631 | 0.303 | 0.631 |
| 2 Weight Groups, Amb&≤30kg=18, NA&≤30kg=24, Amb&>30kg=36, NA&>30kg=42 | 0.261±0.067 | 0.381±0.095 | 0.632 | 0.307 | 0.643 |
| 3 Weight Groups, Amb&≤30kg=18, NA&≤30kg=24, Amb&>30-≤50kg=36, NA&>30-≤50kg=42, Amb&>50=48, NA&>50=54 | 0.261±0.067 | 0.380±0.096 | 0.631 | 0.307 | 0.643 |
| 4 Weight Groups, Amb&≤16kg=12, NA&≤16kg=18, Amb&>16-≤30kg=24, NA&>16-≤30kg=30, Amb&>30-≤50=42, NA&>30-≤50=48, Amb&>50=60, NA&>50=66 | 0.285±0.067 | 0.370±0.097 | 0.633 | 0.320 | 0.668 |

METHODS OF ADMINISTERING DEFLAZACORT THERAPY

TECHNICAL FIELD

The application relates generally to an improved deflazacort therapy and methods for administering novel therapeutic doses of deflazacort.

BACKGROUND

Duchenne muscular dystrophy (DMD) is a recessive, X-linked disorder affecting one in 5000 live male births, making the disorder the most common and most severe form of muscular dystrophy (Mendell et al., 2012). The absence of the protein dystrophin leads to onset of symptoms typically between the ages of 2 to 5 years, with abnormal gait and frequent falls being hallmark signs of the disorder (Koenig et al., 1987; Ciafaloni et al., 2009). Progressive proximal muscle weakness of the legs and pelvis associated with a loss of muscle mass is observed first, with weakness eventually spreading to the arms, neck, and other areas. Other signs may include delays in motor milestones such as sitting, standing independently, climbing and walking, as well as delays in cognitive development. As the condition progresses, wasting occurs in muscle, which is eventually replaced by fat and fibrotic tissue (fibrosis). Untreated patients with DMD will lose ambulation and become wheelchair dependent at a mean age of 9.5 years (Humberclaude et al., 2012). This loss of ambulation due to progressive muscle weakness also leads to a secondary development of musculoskeletal deformity; up to 90% of untreated boys with DMD will develop progressive scoliosis (Bushby et al., 2010). In the second decade of life, complications of respiratory, cardiac, and orthopedic origin are common, with death typically occurring in the second or third decade due to respiratory failure and cardiomyopathy (Eagle et al., 2002). Currently, deflazacort therapy is the only Food and Drug Administration (FDA)-approved treatment available to the entire DMD population. The approved deflazacort therapy is being administered using the standard of care (SOC) weight-based dosing regimen of 0.9 mg/kg/day in patients five years of age and older. The dosing regimen for DMD patients less than five years of age remains to be explored. With earlier diagnoses of DMD being provided for children less than 11 years of age, there remains an opportunity for ensuring such younger patients are administered an effective deflazacort therapy.

SUMMARY

The present disclosure provides an improved deflazacort therapy and methods for administration to all DMD patients, particularly with respect to subjects who are children suffering from DMD. In various aspects, the disclosure provides a deflazacort therapy comprising, administering to a subject suffering from DMD a fixed dose of deflazacort. The effective fixed target dose administered is determined using a combination of one or more factors selected from subject age, weight, ambulatory status or the presence or absence of an inducer or inhibitor of cytochrome P450 3A (CYP3A), in particular, CYP3A4.

In one aspect, the disclosure provides a deflazacort therapy wherein the effective fixed dose to be administered is based on the age of the subject as a factor. In such an aspect, the subject in need thereof is a child or adolescent 18 years of age or younger. In another aspect, the subject is a child (i.e., less than or equal to 11 years of age) and the fixed dose of deflazacort is 6-36 mg per day (e.g., including alternative ranges of 6-12 mg, 6-30 mg, 12-24 mg, 18-24 mg, 20-36 mg or 24-36 mg per day, or having a target dose such as 18 mg or 24 mg per day). In another aspect, the subject is an adolescent (i.e., between 12-18 years of age) and the fixed dose of deflazacort is 30-72 mg per day (e.g., including an alternative range of 30-36 mg, 30-48 mg, 30-54 mg, 36-54 mg, 36-60 mg, 36-72 mg, 42-60 mg, 42-66 mg, 42-72 mg, 48-54 mg, 48-72 mg or 54-72 mg per day, having a target dose such as 36 mg or 42 mg or 48 mg per day). In another aspect, the subject is an adult (i.e., greater than 18 years of age), and the fixed dose of deflazacort is 36-72 mg of deflazacort per day (e.g., including an alternative range of 36-54 mg, 36-60 mg, 42-60 mg, 42-66 mg, 42-72 mg, 48-54 mg, 48-72 mg, 54-60 mg, 54-66 mg, 54-72 mg, 60-66 mg, 60-72 mg or 66-72 mg per day, having a target dose 36 mg, 42 mg, 48 mg, 54 mg, 60 mg, or 66 mg).

In another aspect, the disclosure further provides a deflazacort therapy wherein the effective fixed dose to be administered is based on the weight of the subject as a factor. In such an aspect, the subject in need thereof has a weight that is 30 kg or less and may be administered a fixed dose of deflazacort of 6-36 mg per day (e.g., including an alternative range of 6-12 mg, 6-18 mg, 6-30 mg, 12-18 mg, 12-24 mg, 18-24 mg, 18-30 mg, 18-36 mg, 24-30 mg or 24-36 mg per day, having a target dose such as 18 mg or 24 mg per day). In another aspect, the subject has a weight that is less than or equal to 16 kg, and may be administered a fixed dose of 6-18 mg (e.g., including an alternative range of 6-12 mg or 12-18 mg per day, having a target dose such as 12 mg) of deflazacort per day. In another aspect, the subject has a weight that is greater than 16 kg and less than or equal to 30 kg, and may be administered a fixed dose of 18-36 mg (e.g., including an alternative range of 18-24 mg, 24-30 mg or 24-36 mg per day, having a target dose such as 18, 24 or 30 mg) of deflazacort per day.

In another aspect disclosed herein, the subject has a weight that is greater than 30 kg, and may be administered a fixed dose of deflazacort of 24-96 mg per day (e.g., including alternative ranges of 36-54 mg per day, 36-60 mg per day, 36-96 mg per day, 24-72 mg per day, 36-72 mg per day, 24-48 mg per day, 36-48 mg per day, 42-60 mg per day, 42-66 mg per day, 42-72 mg per day, 42-96 mg per day, 48-54 mg per day, 48-72 mg per day, 48-96 mg per day, 54-72 mg per day or 54-96 mg per day or having a target dose such as 36 mg or 42 mg or 48 mg). In another aspect, the subject has a weight that is greater than 30 kg and less than or equal to 50 kg, and may be administered a fixed dose of 24-66 mg of deflazacort per day (e.g., including alternative ranges of 24-48 mg per day, 24-54 mg per day, 30-42 mg per day, 36-48 mg per day, 36-54 mg per day, 36-60 mg per day, 36-66 mg per day, 42-54 mg per day, 42-60 mg per day, 42-66 mg per day, 42-72 mg per day, 48-54 mg per day, 48-66 mg per day, 48-72 mg per day, 48-96 mg per day, 54-60 mg per day, 54-66 mg per day, 54-72 mg per day or 54-96 mg per day, or having a target dose such as 36 mg per day). In another aspect, the subject has a weight that is greater than 50 kg, and may be administered a fixed dose of 42-96 mg of deflazacort per day (e.g., including alternative ranges of 42-60 mg, 42-66 mg, 48-54 mg, 48-66 mg, 48-96 mg, 48-72 mg, 42-72 mg, 54-66 mg, 54-72 mg or 54-96 mg, or having a target dose such as 48 mg, 54 mg, or 60 mg).

In another aspect, the subject has a weight that is less than or equal to 16 kg, and is ambulatory and may be administered a fixed dose of 6-18 mg (e.g., including an alternative range of 6-12 mg or 12-18 mg per day; or, having a target dose such as 12 mg) of deflazacort per day. In another aspect, the subject has a weight that is less than or equal to 16 kg, and is non-ambulatory and may be administered a fixed dose of 12-24 mg (e.g., including an alternative range of 12-18 mg per day or 18-24 mg per day; or, having a target dose such as 18 mg) of deflazacort per day. In another aspect, the subject has a weight that is greater than 16 kg and less than or equal to 30 kg, and is ambulatory and may be administered a fixed dose of 18-30 mg (e.g., including an alternative range of 18-24 mg or 24-30 mg per day, having a target dose such as 24 mg) of deflazacort per day. In another aspect, the subject has a weight that is greater than 16 kg and less than or equal to 30 kg, and is non-ambulatory and may be administered a fixed dose of 24-36 mg (e.g., including an alternative range of 24-30 mg or 30-36 mg per day, having a target dose such as 30 mg) of deflazacort per day. In another aspect, the subject has a weight that is 30 kg or less and is ambulatory, and may be administered a fixed dose of 12-36 mg per day (e.g., including alternative ranges of 24-36 mg per day, 18-36 mg per day, 18-30 mg per day, 18-24 mg per day, 12-30 mg per day or 12-24 mg per day, or having a target dose such as 18 mg per day). Alternatively, the subject has a weight that is 30 kg or less is non-ambulatory, and may be administered a fixed dose of 18-54 mg per day (e.g., including alternative ranges of 18-36 mg per day, 18-30 mg per day, 18-24 mg per day, 24-36 mg per day, 24-48 mg per day or 24-54 mg per day, or having a target dose such as 24 mg per day).

In another aspect, the subject has a weight that is greater than 30 kg and is ambulatory, and may be administered a fixed dose of deflazacort of 24-60 mg per day (e.g., including alternative ranges of 24-48 mg per day, 24-54 mg per day, 30-42 mg per day, 36-48 mg per day, 36-54 mg per day, 36-60 mg per day, 36-66 mg per day, 42-54 mg per day, 42-60 mg per day, 48-54 mg per day, 48-60 mg per day or 54-60 mg per day or having a target dose such as 36 mg per day). In another aspect, the subject has a weight that is greater than 30 kg and is non-ambulatory, and may be administered a fixed dose of deflazacort of 30-72 mg per day (e.g., including an alternative range of 30-36 mg per day, 30-42 mg per day, 30-48 mg per day, 30-54 mg per day, 36-48 mg per day, 36-54 mg per day, 36-72 mg per day, 42-54 mg per day, 42-60 mg per day, 42-66 mg per day, 48-54 mg per day or 54-72 mg per day, or having a target dose such as 42 mg per day). In another aspect, the subject has a weight greater than 30 kg and less than or equal to 50 kg and is ambulatory, the fixed dose of deflazacort administered may be 24-54 mg per day (e.g., including an alternative range of 24-48 mg per day, 30-42 mg per day, 36-48 mg per day, 36-54 mg per day, 36-66 mg per day, 42-54 mg per day, 42-60 mg per day or 48-54 mg per day, or having a target dose such as 36 mg per day); if the subject having a weight greater than 30 kg and less than or equal to 50 kg is non-ambulatory, the fixed dose of deflazacort is 30-66 mg per day (e.g., including an alternative range of 30-36 mg per day, 30-60 mg per day, 36-54 mg per day, 36-60 mg per day, 42-54 mg per day, 42-60 mg per day, 42-66 mg per day, 48-54 mg per day, 48-66 mg per day or 54-66 mg per day, or having a target dose such as 42 mg per day). In another aspect, the subject has a weight that is greater than 50 kg, the fixed dose of deflazacort administered may be 48-72 mg per day (e.g., including an alternative range of 48-54 mg per day, 48-60 mg per day, 48-66 mg per day, 54-60 mg per day, 54-66 mg per day or 54-72 mg per day, or having a target dose such as 48 mg per day or 54 mg per day) if ambulatory; if the subject having a weight greater 50 kg is non-ambulatory, the fixed dose of deflazacort administered may be 54-96 mg per day (e.g., including an alternative range of 54-90 mg per day, 60-90 mg per day, 66-84 mg per day or 72-96 mg per day, or having a target dose such as 54 mg or 66 mg per day).

In another aspect, the subject is a child (i.e., less than or equal to 11 years of age) and is ambulatory and may be administered a fixed dose of 6-18 mg of deflazacort per day (e.g., including alternative ranges of 6-12 mg or 12-18 mg per day, or having a target dose such as 18 mg per day). In another aspect, the subject is a child and is non-ambulatory, and may be administered a fixed dose of 12-30 mg of deflazacort per day (e.g., including alternative ranges of 12-18 mg, 12-24 mg, 18-24 mg or 18-30 mg per day, or having a target dose such as 18 mg or 24 mg per day). In another aspect, the subject is an adolescent (i.e., greater than 11 years of age) and is ambulatory and may be administered a fixed dose of 30-60 mg of deflazacort per day (e.g., including alternative ranges of 30-36 mg, 30-48 mg, 36-54 mg, 36-54 mg, 36-60 mg, 42-60 mg, 48-54 mg or 48-60 mg, per day, or having a target dose such as 36 mg per day). In another aspect, the subject is an adolescent and is non-ambulatory, and may be administered a fixed dose of 36-72 mg of deflazacort per day (e.g., including alternative ranges of 36-54 mg, 36-60 mg, 36-66 mg, 42-54 mg, 42-60 mg, 42-66 mg, 42-72 mg, 48-54 mg, 48-60 mg, 48-66 mg or 48-72 mg, per day, or having a target dose such as 36 mg or 42 mg per day). In another aspect, the subject is an adult (i.e., greater than 18 years of age) and is ambulatory and may be administered a fixed dose of 36-72 mg of deflazacort per day (e.g., including alternative ranges of 36-54 mg, 36-60 mg, 42-60 mg, 42-66 mg, 42-72 mg, 48-54 mg, 48-72 mg, 54-60 mg, 54-66 mg or 54-72 mg per day, or having a target dose such as 42 mg per day). In another aspect, the subject is an adult and is non-ambulatory, and may be administered a fixed dose of deflazacort of 48-96 mg per day (e.g., including alternative ranges of 48-54 mg, 48-60 mg, 48-72 mg, 54-60 mg, 54-72 mg or 54-96 mg per day, or having a target dose such as 54 mg, or 66 mg).

In any of the aspects described herein, the deflazacort therapy may comprise administering the fixed dose daily, on alternative days, two consecutive days per week, or for a period of time followed by a dosing reprieve (e.g., administering the fixed dose each day for ten days, not administering deflazacort for the following ten days, then optionally resuming administration). When dosing on alternative days, the deflazacort fixed dose is about the same as the daily dose or is double (two-times; 2×) the daily dose for the aspects described herein. When dosing two days per week, the deflazacort fixed dose is three to ten times (e.g., six times; 6×) the daily dose in any of the aspects described herein. For example, when deflazacort is administered only two days per week (e.g., "high dose weekend"), the deflazacort therapy may comprise administering a fixed dose of 24-360 mg per day for two days followed by a five day dosing reprieve. When deflazacort is given for a period of time followed by a dosing reprieve of similar length (e.g., administered for ten days, then not administered for ten days), the dose is about the same or optionally up to three times higher than the daily dose of any of the aspects described herein.

In one aspect, the disclosure further provides a deflazacort therapy that may be administered to a subject suffering from DMD, comprising increasing the dosage administered to the subject when the subject loses ambulation. In another aspect, the therapy comprises increasing the dosage by about 6 mg to about 24 mg (e.g., about 6 mg to about 12 mg or about 12 mg to about 24 mg) per administration (e.g., administration per day). In another aspect, the therapy comprises increasing the dosage in the subject by 1.2 fold or 1.4 fold. Put another way, the fixed deflazacort dose for a non-ambulatory subject is 1.2 to 1.4 times higher than an ambulatory subject with the same weight.

In one aspect, the deflazacort therapy comprises administering to a subject in need a therapeutically effective amount of deflazacort and avoiding, discontinuing, or contraindicating administration of a cytochrome P450 3A (CYP3A) (e.g., CYP3A4) inducer. In another aspect, the deflazacort therapy comprises increasing the dosage of deflazacort administered to the subject during concomitant administration of a CYP3A (e.g., CYP3A4) inducer. In another aspect, the deflazacort therapy to a subject in need thereof comprises decreasing the dosage of deflazacort administered to the subject during concomitant administration of a CYP3A (e.g., CYP3A4) inhibitor. Such aspects contemplate that the CYP3A4 inducer may be a moderate CYP3A4 inducer, or a strong CYP3A4 inducer; and that the CYP3A4 inhibitor may be a moderate CYP3A4 inhibitor, or a strong CYP3A4 inhibitor.

The disclosure further provides a deflazacort therapy for the treatment of a subject suffering from DMD, such as a subject 18 years or younger. In some aspects, the deflazacort therapy is administered as a fixed dose (e.g., any of the fixed doses disclosed herein). In other aspects, the fixed dosage of deflazacort is increased when the subject loses ambulation. In certain aspects, a therapeutically effective amount of deflazacort is administered and administration of a CYP3A inducer is avoided. In certain aspects, the fixed dosage of deflazacort administered to the subject is increased during concomitant administration of a CYP3A inducer. In certain aspects, a therapeutically effective amount of deflazacort is administered and administration of a CYP3A inhibitor is avoided. In certain aspects, the fixed dosage of deflazacort administered to the subject is reduced during concomitant administration of a CYP3A inhibitor.

DESCRIPTION OF THE FIGURES

FIG. 17 is a table summarizing simulations of fixed dosing regimens (regardless of ambulatory status). The mean change in muscle strength at 12 weeks, the mean change in muscle strength at 52 weeks, the proportion of 52 week forced vital capacity (FVC) responders, the proportion of subjects with weight gain at 52 weeks, and the proportion of subjects with Cushingoid Syndrome at 52 weeks are presented for each dosing regimen, assuming 50 subjects per arm.

FIG. 18 is a table summarizing simulations of fixed dosing regimens (by ambulatory status). The mean change in muscle strength at 12 weeks, the mean change in muscle strength at 52 weeks, the proportion of 52 week FVC responders, the proportion of subjects with weight gain at 52 weeks, and the proportion of subjects with Cushingoid Syndrome at 52 weeks are presented for each dosing regimen, assuming 50 subjects per arm.

DETAILED DESCRIPTION

Figure 1:
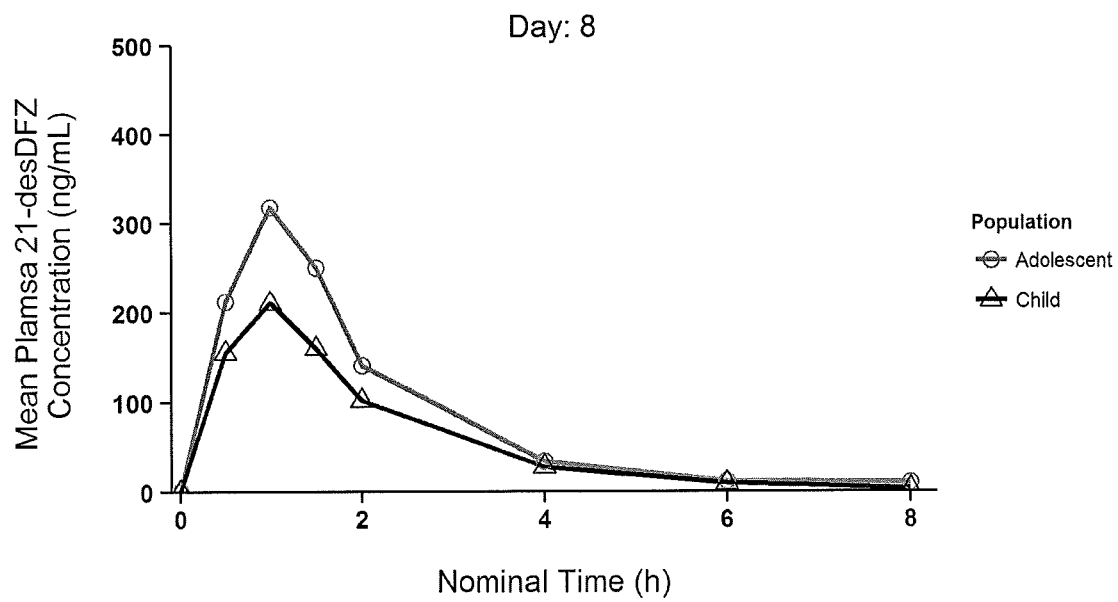
FIG. 1 is a line graph illustrating mean plasma 21-desDFZ (active deflazacort metabolite) concentration (ng/mL; y-axis) vs. time (hours; x-axis) overlaid by study population on Day 8 (linear scale; circles=adolescent; triangles=child). Children (ages 5-11, inclusive) and adolescents (ages 12-16, inclusive) were administered the weight-based regimen of 0.9 mg/kg/day deflazacort orally once daily for 8 days. Blood samples were collected through eight hours postdose. Blood samples were processed to plasma and concentrations of 21-desDFZ were measured using validated bioanalytical assays. The difference in mean plasma concentration of 21-desDFZ resulting from weight-based dosing in children and adolescents is demonstrated in the first four hours following administration. At about one hour following administration, children exhibit only 67% of the mean plasma concentration observed in adolescents.

The disclosure provides an improved deflazacort therapy for administration to subjects in need thereof. Features of the therapy are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the therapy described herein can be deleted, combined with, or substituted for, in whole or part, any other feature described herein.

Deflazacort, also known as (11β,16β)-21-(acetyloxy)-11-hydroxy-2'-methyl-5'H-pregna-1,4-dieno[17,16-d]oxazole-3,20-dione, is a glucocorticoid (GC) used as an anti-inflammatory and immunosuppressive agent. Pharmacologically, it is a pro-drug which is metabolized rapidly and completely in the plasma by esterases to the active drug 21-desacetyldeflazacort (21-desDFZ). After oral administration, GCs such as deflazacort or prednisone are readily absorbed into the bloodstream. GCs diffuse through cell membranes to the cytoplasm to bind soluble steroid hormone receptors that dimerize and translocate to the nucleus. In the nucleus, the receptor complex directly binds promoter elements that modulate gene transcription. The intracellular GC receptor (GR) binds GC Response Elements (GREs) in target gene promoters that can activate or inhibit transcription of a variety of genes. Downstream effects of GCs include increase in myoblast growth and stabilization of muscle fiber membranes, followed by reduction in muscle necrosis. GCs can also suppress the inflammatory process by inhibiting production of inflammatory mediators, such as arachidonic acid metabolites, cytokines, interleukins, adhesion molecules, and enzymes, and by affecting B cell activity.

The American Academy of Neurology (AAN) and Center for Disease Control (CDC) guidelines recommend glucocorticoids (including prednisone or deflazacort) as first line therapy at the time of DMD diagnosis, typically ages 4-5. Treatment is generally aimed at controlling the symptoms and modifying certain aspects of the disease to sustain and maximize muscle function and improve quality of life. Results from multiple studies presented in Manzur et al. (2008) showed that glucocorticoids improve muscle strength, which was maximal at 3 months and maintained up to 18 months. Increases in muscle strength were paralleled by significant improvements in functional testing and muscle mass, as measured by urinary creatinine excretion.

Applicants observed that deflazacort improves muscle strength in both ambulatory and non-ambulatory patients as early as six weeks after treatment initiation, that improvements in muscle strength are preserved during long-term treatment up to 24-months, that increases in muscle strength are paralleled by significant improvements in functional testing and muscle mass (as measured by urinary creatinine excretion), and also by improvements in pulmonary function testing.

Standard of Care (SOC) dosing of corticosteroids to DMD patients has been based on patient weight (mg/kg), regardless of the dosing schedule (daily; alternate day; 10 days on, 10 days off; high-dose weekends only; etc.), age, ambulatory status, use of CYP inducers or inhibitors and the like. The recommended SOC dose of deflazacort in DMD patients has been selected from 0.9 mg/kg or 1.2 mg/kg. In various aspects, the therapeutic dose is 0.9 mg/kg/day. In various aspects of the present disclosure, the therapeutically effective amount is other than 0.9 mg/kg or 1.2 mg/kg. The recommended dose is based on clinical data from randomized, blinded, placebo-controlled trials with additional supportive evidence obtained from the global literature, as well as clinical standard of care guidelines for treatment. The widespread adoption and acceptance of weight-based (mg/kg) dosing is highlighted by Bello et al. (2015), where the authors published findings from a long-term observational, natural history study of boys with DMD treated with prednisone/prednisolone or deflazacort. In 340 participants, there were fourteen different weight-based (mg/kg) dosing regimens recorded.

In one aspect, the dosing schedule comprises, a scheduled period selected from administering the fixed dose daily; or, administering twice the daily fixed dose on alternate days; or, administering thrice the daily fixed dose on each of 10 days followed by 10 days with no fixed dose administration; or, administering thrice to five times the daily fixed dose on each of 2 days followed by 5 days with no fixed dose administration.

In another aspect, the dosing schedule comprises, administering the fixed dose for a plurality of scheduled periods. In another aspect, the fixed dose may be reduced by 6 mg for each period until a lower fixed dose of deflazacort is being administered or until deflazacort therapy has been completely discontinued. In this aspect, the lower fixed dose or discontinuance of deflazacort therapy may be required due to development of intolerability or adverse events. In another aspect, the fixed dose reduction by 6 mg for each period may continue until the intolerability or adverse events are mitigated; whereupon, therapy may continue at a lower fixed dose.

Fixed Dose Regimen

Figure 4:
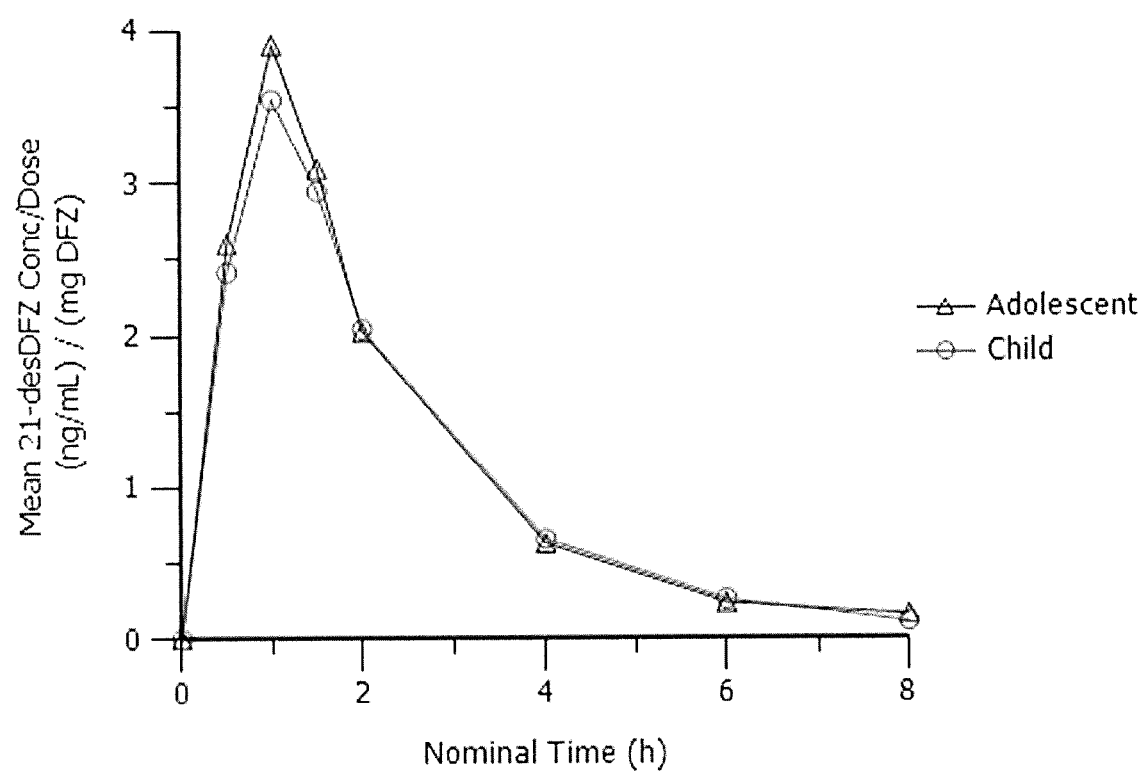
FIG. 4 is a line graph correlating mean dose-normalized 21-desDFZ concentration (ng/mL; y-axis) and time (hours) by study population (triangles=adolescent; circles=child). The figure illustrates data from Day 8. Corrected for dose, there are negligible differences in the concentration-time profiles of 21-desDFZ between children and adolescents.
Figure 5:
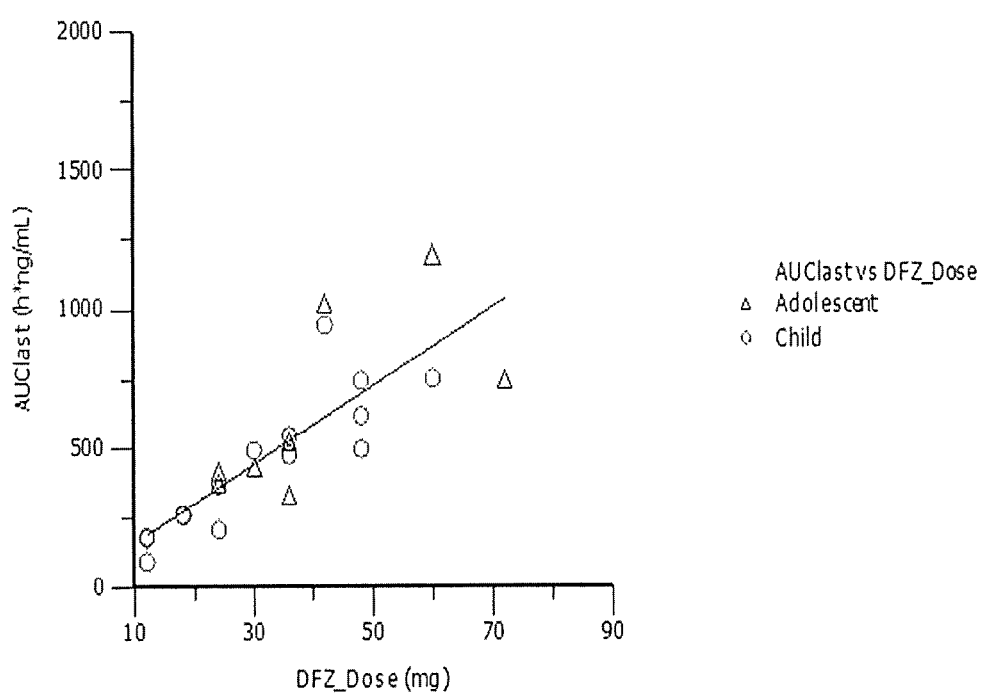
FIG. 5 is a scatter plot of 21-desDFZ AUC as a function of dose on Day 8 based on data from a deflazacort pharmacokinetic study in child DMD subjects (aged 5 to 11 years old) and adolescent DMD subjects (aged 12 to 16 years old). The scatterplot of AUC (h*ng/mL; y-axis) vs. dose (mg; x-axis) demonstrate a tight linear relationship regardless of the subject population, with exposures in both child and adolescent subjects increasing in a similar manner as shown by comparable regression slopes. These data suggest a trend toward increasing exposure ($C_{max}$ and AUC) with increasing age that may be better explained as a function of actual dose administered rather than age alone. In other words, regardless of patient subpopulation (children or adolescent), dose-normalized total exposures to 21-desDFZ as measured by AUC correlate with the total weight based dose actually received and are not complicated by age or maturation of metabolizing enzymes. Accordingly, these data clearly show that, with a target dose regimen of 0.9 mg/kg/day, child subjects were consistently under-dosed compared to adolescent subjects.
Figure 6:
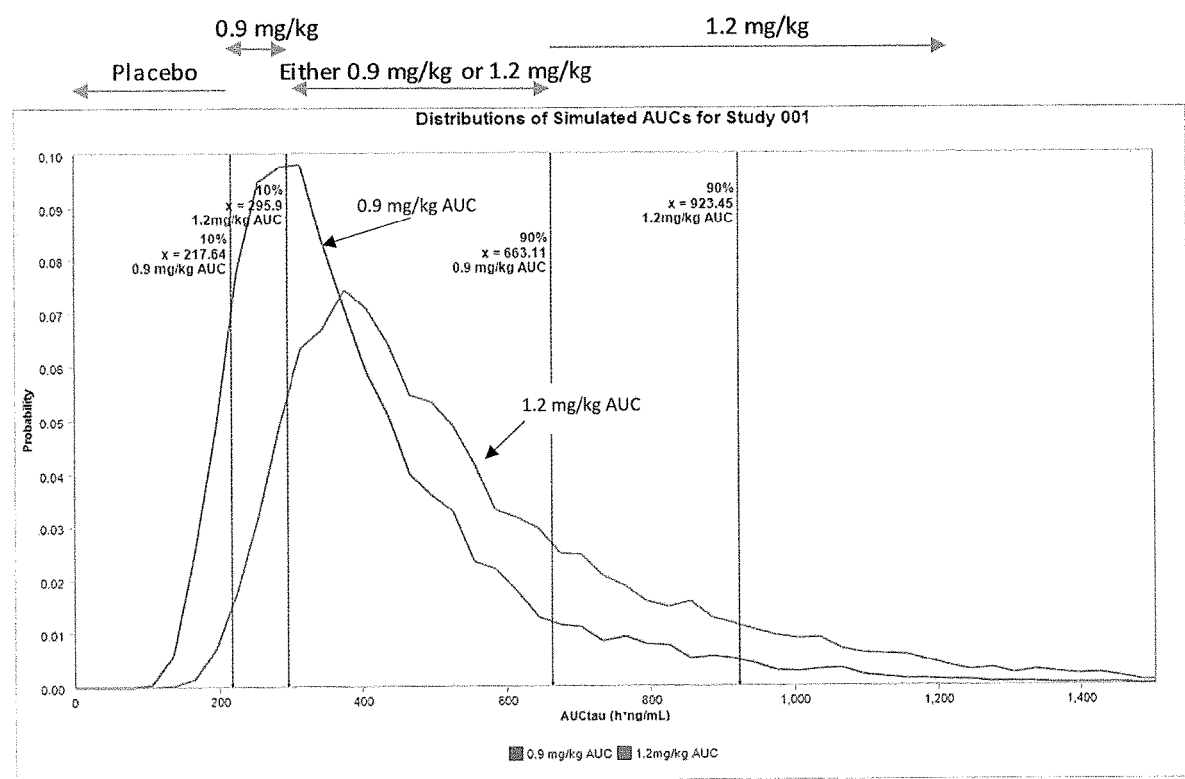
FIG. 6 is a histogram of the predicted AUC after deflazacort 0.9 mg/kg and 1.2 mg/kg as simulated in patients with DMD from clinical efficacy studies with deflazacort. The clinical simulation pharmacokinetic modeling data derived from pharmacokinetic and pivotal clinical efficacy studies indicate substantial overlap in estimated exposures to the 21-desDFZ metabolite using the SOC dosing regimen of 0.9 and 1.2 mg/kg/day, where the 10th and 90th percentiles for each dose are highlighted. The bars with arrows above the graph show the doses that were assumed for given exposures.

Surprisingly, an investigation of the pharmacokinetics of 21-desDFZ after oral administration of deflazacort to children and adolescents with DMD (see, Griggs, et al) revealed that the standard-of-care weight-based (mg/kg) dosing is not optimal for children whose age inherently correlates with a lower weight (for whom the Current Dosing Table does not provide any coverage) and adolescents who have become non-ambulatory (for whom the Current Dosing Table also does not provide any coverage). We have discovered that young patients (those having an age less than or equal to 11 years old) and non-ambulatory adolescents (those having an age greater than 11 years old and less than or equal to 18 years old) are at risk for the greatest variance in total dose administered in relation to the weight-based SOC target dose shown in the Current Dosing Table (see Table 1c). Analysis of the total doses of deflazacort administered to the youngest children with DMD (those of which are also predisposed to having the lowest weight) demonstrated that a considerable number of patients in this subpopulation were under-dosed (FIG. 1 and FIG. 5). While plasma concentrations were lower in such children (regardless of ambulatory status) compared to adolescents (regardless of ambulatory status) receiving deflazacort using a weight-based dosing regimen of 0.9 mg/kg once daily for 8 days, the dose normalized plasma concentrations were similar for the absolute dose the subjects received (FIG. 4). The clinical trial simulations described herein were conducted to extrapolate the 21-desDFZ concentrations from the actual clinical data, showing that exposure is unexpectedly more dependent on a fixed dose than on either the current standard of care weight-based dosing regimen or even a theoretical weight-based (mg/kg) dose administered. Using the area under the plasma concentration time curve during a dosing interval (AUC) corrected for dose and subject body weight (FIG. 6), the AUC could be predicted for a weight-based deflazacort 0.9 mg/kg and 1.2 mg/kg dose, as administered in the pivotal, efficacy and safety clinical trial. In contrast to dose response studies suggesting a difference in plasma concentration between 0.9 mg/kg and 1.2 mg/kg, there is actually a substantial overlap in exposure between these two doses (FIG. 6). However, these doses are unexpectedly relatively equivalent when concentrations are normalized to the actual deflazacort dose administered (in mg) to each subject (FIG. 6).

Thus, a fixed dose of deflazacort has the potential for reducing the complexity of the Current Dosing Table 1c used presently by physicians, while enhancing efficacy and providing a more appropriate/effective dose when multiple factors (other than just weight) are considered. The modeling data used to derive the fixed-dose ranges suggest that in addition to weight, the subject age, ambulatory status and CYP inducer/inhibitor usage must also be considered as factors in patient population subgroups to determine an effective fixed dose regimen (as shown in Table 1).

The clinical trial simulations were conducted assuming the efficacy and safety of different fixed doses of deflazacort as compared to weight-based dosing of prednisone 0.75 mg/kg/day and placebo, along with the original results from weight-based dosing of deflazacort 1.2 mg/kg/day and deflazacort 0.9 mg/kg/day, to develop simpler fixed dose regimens that would produce similar efficacy and safety to the Current Dosing Table currently used by physicians. The fixed dose regimen and other aspects described herein were developed based on these clinical trial simulations. The disclosure provides, in these aspects, a simplified, fixed-dose regimen that provides more appropriate exposures to the active metabolite of deflazacort, 21-desDFZ, in children, adolescents, and adults, while employing a simpler dosing regimen. This disclosure also provides, in other aspects, differential dosing for ambulatory adolescents as the loss of ambulation accelerate at around age 15 due to progressive muscle degeneration and loss of muscle tissue. Data from simulated clinical trials revealed that the fixed dose for a non-ambulatory adolescent should be increased as the loss of ambulation accelerates and continued post-ambulation, rather than "capped" or reduced as is current, clinical practice.

Other aspects of the deflazacort therapy described herein comprise administering to a subject suffering from Duchenne muscular dystrophy (DMD) a fixed dose of deflazacort. The term "fixed dose" is meant to describe a dosage that is not calculated by a daily weight-based formula (i.e., as mg/kg/day or according to the Current Dosing Table). The particular fixed dose of deflazacort to be administered is selected based on at least one or more of a plurality of factors, e.g., age of the subject, weight of the subject, ambulation status, and CYP inducer/inhibitor usage. While each of these factors may have some overlapping pharmacokinetic effect with each other based on certain subject phenotypes, they are connected such that an effect on one has a multiplied effect on others. For example, depending on the amount of body fat present and height, subject weight will affect body surface area (which affects cardiac output and liver volume, liver weight and the amount of microsomal protein in milligrams per gram of liver, thus affecting intrinsic liver clearance). At the same time, subject age affects height and the corresponding amount of body fat (which affects body surface area and corresponding liver volume and liver weight), as well as the amount of microsomal protein in milligrams per gram of liver (thus affecting intrinsic liver clearance), cardiac output and serum creatinine levels. Categorizing subjects based on other factors besides weight alone for selecting and administering a deflazacort therapy using a fixed dosage regimen is a departure from the Current Dosing Table daily weight-based dosing (at 0.9 mg/kg/day or 1.2 mg/kg/day), the standard of care used in deflazacort treatment regimens. In other aspects of the fixed dose deflazacort therapy described herein, subjects in a particular weight class are administered a fixed dosage, which does not require recalculation of dose (at 0.9 mg/kg/day or 1.2 mg/kg/day) each time a subject's weight incrementally changes. Based on the clinical trial simulation modeling data described herein, a fixed dose regimen has the advantage of providing a more appropriate 21-desDFZ exposure to a child or npn-ambulatory adolescent.

In one aspect, the fixed dose of deflazacort is preferably 100 mg or less (e.g., 72 mg or less) per administration (e.g., per day). In certain aspects wherein the subject is a child (i.e., less than or equal to 11 years of age, having an age in a range such as 2-11 years or 4-11 years), the fixed dose of deflazacort to be administered is preferably 6-36 mg per day (e.g., including alternative ranges of 6-12 mg, 18-24 mg, 6-30 mg, 12-24 mg, 20-36 mg, 24-36 mg, or having a target dose such as 24 mg per day). In other aspects, the subject is an adolescent (i.e., having an age in a range such as greater than 11-18 years of age), and the fixed dose of deflazacort to be administered is 30-72 mg per day (e.g., including alternative ranges of 36-72 mg, 42-66 mg, 48-54 mg, or having a target dose such as 48 mg, or 42 mg per day). In other aspects, the subject is an adult (i.e., having an age greater than 18 years of age), and the fixed dose of deflazacort to be administered is 36-96 mg per day (e.g., including alternative ranges of 36-72 mg, 54-96 mg, 60-90 mg, 66-84 mg, 72-96 mg, or having a target dose such as 48 mg, 54 mg, 60 mg, or 66 mg).

In another aspect, the subject to be administered deflazacort therapy has a weight that is 30 kg or less, and the fixed dose of deflazacort to be administered is 6-36 mg per day (e.g., including alternative ranges of 16-36 mg, 18-24 mg, 24-36 mg, or having a target dose such as 18 mg, or 24 mg). In other aspects, the population of subjects 30 kg or less can be stratified into two subpopulations based on weight: (i) subjects having a weight less than or equal 16 kg may be administered a fixed dose of 6-18 mg (e.g., including alternate ranges of 6-12 mg, 12-18 mg, or having a target dose such as 12 mg) of deflazacort per day; and (ii) subjects having a weight greater than 16 kg and less than or equal to 30 kg may be administered a fixed dose of 18-36 mg (e.g., including an alternate range of 18-24 mg, 24-30 mg, 24-36 mg, or having a target dose such as 24 mg or 30 mg) per day.

In another aspect, the subject has a weight that is greater than 30 kg, and the fixed dose of deflazacort to be administered is 24-96 mg per day (e.g., including alternative ranges of 24-72 mg, 24-48 mg, having a target dose such as 36 mg, or 42 mg). In other aspects, the population of subjects greater than 30 kg can be further stratified to generate two subpopulations based on weight: (i) subjects having a weight greater than 30 kg and less than or equal to 50 kg may be administered a fixed dose of 24-66 mg per day (e.g., including alternative ranges of 24-54 mg, 24-48 mg, 30-42 mg, 36-54 mg, or having a target dose such as 36 mg) of deflazacort, and (ii) subjects having a weight greater than 50 kg may be administered a fixed dose of 48-96 mg per day (e.g., including alternative ranges of 48-72 mg, 54-66 mg, or having a target dose such as 48 mg, 54 mg, or 54 mg) of deflazacort.

In one aspect, the deflazacort therapy for administration to a subject that is suffering from Duchenne muscular dystrophy (DMD) comprises, determining a fixed target dose range of deflazacort to be administered to the subject using one or more factors selected from the subject's age, weight and ambulatory status; wherein the subject's age is selected from an age less than or equal to 11 years of age, an age greater than 11 years to less than or equal to 18 years of age or an age greater than 18 years of age, wherein the subject's weight is selected from a weight less than or equal to 30 kg, a weight greater than 30 kg to less than or equal to 50 kg or a weight greater than 50 kg, wherein the subject's ambulatory status is selected from ambulatory or non-ambulatory, and wherein the selection of factors determine the fixed target dose range to administer; administering a target dose from the fixed target dose range; and measuring a treatment, amelioration or prevention of DMD symptoms selected from improved muscle strength, response time to a timed function test and improvement in pulmonary function in the subject.

In another aspect, the subject age range is less than or equal to 11 years of age and the fixed target dose range of deflazacort is 6-36 mg per day, having a target dose of 18 or 24 mg per day; or, the age range is greater than 11 years of age and less than or equal to 18 years of age and the fixed target dose range of deflazacort is 30-72 mg per day, having a target dose of 36, 42 or 48 mg per day; or, an age range of greater than 18 years of age and the fixed target dose range of deflazacort is 36-72 mg per day, having a target dose of 36, 42, 48, 54, 60 or 66 mg per day.

In another aspect, the fixed target dose range of deflazacort for a subject less than or equal to 11 years of age is selected from 6-18 mg per day, having a target dose of 18 mg per day for an ambulatory subject or, 12-30 mg per day, having a target dose of 18 or 24 mg per day for a non-ambulatory subject; or, wherein the fixed target dose range of deflazacort for a subject greater than 11 years of age and less than or equal to 18 years of age is selected from 30-60 mg per day, having a target dose of 36 mg per day for an ambulatory subject or, 36-72 mg per day, having a target dose of 36 or 42 mg per day for a non-ambulatory subject; or, wherein the fixed target dose range of deflazacort for a subject greater than 18 years of age is selected from 36-72 mg per day, having a target dose of 42 mg per day for an ambulatory subject or, 48-96 mg per day, having a target dose of 54 or 66 mg per day for a non-ambulatory subject.

In another aspect, the subject weight range is less than or equal to 30 kg and the fixed target dose range of deflazacort is 6-36 mg per day, having a target dose of 18 or 24 mg per day; or, the subject weight range is greater than 30 kg and less than or equal to 50 kg and the fixed target dose range of deflazacort is 24-66 mg per day, having a target dose of 36 mg per day; or, the subject weight range is greater than 50 kg and the fixed target dose range of deflazacort is 42-96 mg per day, having a target dose of 48, 54 or 60 mg per day.

In another aspect, the fixed target dose range of deflazacort for a subject weight range less than or equal to 30 kg is selected from 12-36 mg per day, having a target dose of 18 mg per day for an ambulatory subject or, 18-54 mg per day, having a target dose of 24 mg per day for a non-ambulatory subject; or, wherein the fixed target dose range of deflazacort for a subject weight range greater than 30 kg and less than or equal to 50 kg is selected from 24-60 mg per day, having a target dose of 36 mg per day for an ambulatory subject or 30-72 mg per day, having a target dose of 42 mg per day for a non-ambulatory subject; or, wherein the fixed target dose range of deflazacort for a subject weight range greater than 50 kg is selected from 48-72 mg per day, having a target dose of 48 mg per day for an ambulatory subject or, 54-96 mg per day, having a target dose of 54 mg per day for a non-ambulatory subject.

In another aspect, the target dose selected from a fixed target dose range of deflazacort for a subject less than or equal to 11 years of age and having a subject weight range less than or equal to 30 kg is selected from 18 mg per day for an ambulatory subject or, 24 mg per day for a non-ambulatory subject; or, wherein the target dose selected from a fixed target dose range of deflazacort for a subject greater than 11 years of age and less than or equal to 18 years of age and having a subject weight range greater than 30 kg and less than or equal to 50 kg is selected from 36 mg per day for an ambulatory subject or, 42 mg per day for a non-ambulatory subject; or, wherein the target dose selected from a fixed target dose range of deflazacort for a subject greater than 18 years of age and having a subject weight range greater than 50 kg is selected from 48 mg per day for an ambulatory subject or, 54 mg per day for a non-ambulatory subject.

In addition to providing fixed dose regimens for subjects based on age or weight classification, the disclosure provides for improved regimens based on ambulatory status, depending on use of a CYP inducer or inhibitor. Ambulatory status and usage of CYP inducers or inhibitors are described further below. Exemplary fixed dose regimens are provided in Table 1, which is provided merely to illustrate various aspects of the disclosure and is not meant to be limiting. In the various aspects shown in Table 1 and described herein, an exemplary dose range, alternative range and target dose are provided for each subject classification based on age or weight, these classifications are further stratified based on ambulatory (Amb) or non-ambulatory (Non-Amb) status, having a corresponding dose range, alternative range and target dose for each; and, when fixed dose deflazacort therapy is administered in the presence of a CYP inhibitor (CYP Inh), the dose range and target dose represent a 3-4 fold decrease in the dose range and target dose for each classification, where applicable; or, when therapy is administered in the presence of a CYP inducer (CYP Ind), the dose range and target dose represent a 3-4 fold increase in the dose range and target dose for each classification, where applicable.

TABLE 1

| Dose (mg) | Age (years old) | | | Weight (kg) | | | | | |
| --- | --- | --- | --- | --- | --- | --- | --- | --- | --- |
| | ≤11 | >11-18 | >18 | ≤16 | >16-≤30 | ≤30 | >30 | >30-≤50 | >50 |
| Exemplary | 6-36 | 30-72 | 36-72 | 6-18 | 18-36 | 6-36 | 24-96 | 24-66 | 42-96 |
| | 6-12, | 30-36, | 36-54, | 6-12, | 18-24, | 6-12, | 24-48, | 24-48, | 42-60, |
| | 6-30, | 30-48, | 36-60, | 12-18 | 24-30, | 6-18, | 24-72, | 24-54, | 42-66, |
| | 12-24, | 30-54, | 42-60 | | 24-36 | 6-30, | 36-48, | 30-42, | 42-72, |
| | 18-24, | 36-54, | 42-66, | | | 12-18, | 36-54, | 36-48, | 48-54, |
| | 20-36, | 36-60, | 42-72, | | | 12-24, | 36-60, | 36-54, | 48-66, |
| | 24-36 | 36-72, | 48-54, | | | 18-24, | 36-72, | 36-60, | 48-72, |
| | | 42-60, | 48-72, | | | 18-30, | 36-96, | 36-66, | 48-96, |
| | | 42-66, | 54-60, | | | 18-36, | 42-60, | 42-54, | 54-60, |
| | | 42-72, | 54-66, | | | 24-30, | 42-66, | 42-60, | 54-66, |
| | | 48-54, | 54-72, | | | 24-36 | 42-72, | 42-66, | 54-72, |
| | | 48-72, | 60-66, | | | | 42-96, | 48-54, | 54-96 |
| | | 54-72 | 60-72, | | | | 48-54, | 48-66, | |
| | | | 66-72 | | | | 4872, | 54-60, | |
| | | | | | | | 48-96, | 54-66 | |

TABLE 1-continued

| Dose (mg) | Age (years old) | | | Weight (kg) | | | | | |
|---|---|---|---|---|---|---|---|---|---|
| | ≤11 | >11-18 | >18 | ≤16 | >16-≤30 | ≤30 | >30 | >30-≤50 | >50 |
| Target | 18, 24 | 36, 42, 489 | 36, 42, 48, 54, 60, 66 | 12 | 18, 24, 30 | 18, 24 | 36, 42, 48 | 36 | 54-72, 54-96 48, 54, 60 |
| Amb Range | 6-18 | 30-60 | 36-72 | 6-18 | 18-30 | 12-36 | 24-60 | 24-54 | 48-72 |
| Alternative Range | 6-12, 12-18 | 30-36, 30-48, 30-54, 36-54, 36-48, 36-60, 42-60, 48-54, 54-60 | 36-54, 36-60, 42-60, 42-66, 42-72, 48-54, 48-72, 54-60, 54-66, 54-72 | 6-12, 12-18 | 18-24, 24-30 | 12-24, 12-30, 18-24, 18-30, 18-36, 24-36 | 24-48, 24-54, 30-42, 36-48, 36-54, 36-60, 36-66, 42-54, 42-60, 48-54, 48-60, 54-60 | 24-48, 30-42, 36-48, 36-54, 36-66, 42-54, 42-60, 48-54, | 48-54, 48-60, 48-66, 54-60, 54-66, 54-72 |
| Amb Target | 18 | 36 | 42 | 12 | 24 | 18 | 36 | 36 | 48, 54 |
| Non-Amb Range | 12-30 | 36-72 | 48-96 | 12-24 | 24-36 | 18-54 | 30-72 | 30-66 | 54-96 |
| Alternative Range | 12-18, 12-24, 18-24, 18-30 | 36-54, 36-60, 36-66, 42-54, 42-60, 42-66, 42-72, 48-54, 48-60, 48-66, 48-72 | 48-54, 48-60, 48-72, 54-60, 54-72, 54-96 | 12-18, 18-24 | 24-30, 30-36 | 18-24, 18-30, 18-36, 24-36, 24-48, 24-54 | 30-36, 30-42, 30-48, 30-54, 36-48, 36-54, 36-72, 42-54, 42-60, 42-66, 48-54, 54-72 | 30-36, 30-60, 36-54, 36-60, 42-54, 42-60, 42-66, 48-54, 48-66, 54-66 | 54-90, 60-90, 66-84, 72-96 |
| Non-Amb Target | 18, 24 | 36, 42 | 54, 66 | 18 | 30 | 24 | 42 | 42 | 54, 66 |
| CYP Inh Range | | | | | | | | | |
| Exemplary Target | 6-12 | 12-24 | 12-32 | 6-12 | 6-12 | 6-12 | 12-32 | 12-32 | 12-32 |
| | 6 | 12 | 18 | 6 | 6 | 6 | 18 | 18 | 18 |
| Amb Range | 6-12 | 6-18 | 12-24 | 6-12 | 6-12 | 6-18 | 6-18 | 6-18 | 12-24 |
| Amb Target | 6 | 12 | 18 | 6 | 6 | 12 | 12 | 12 | 18 |
| Non-Amb Range | 12-18 | 12-24 | 54-96 | 6-12 | 6-12 | 6-12 | 6-18 | 6-12 | 18-24 |
| Non-Amb Target | 12 | 18 | 54 | 12 | 12 | 12 | 12 | 12 | 18 |
| CYP Ind Range | | | | | | | | | |
| Exemplary Target | 18-108 | 90-216 | 108-288 | 18-54 | 54-108 | 18-108 | 72-288 | 72-198 | 126-288 |
| | 66 | 162 | 198 | 36 | 84 | 66 | 180 | 138 | 210 |
| Amb Range | 18-48 | 90-162 | 108-216 | 18-48 | 18-48 | 54-72 | 72-108 | 108-144 | 144-192 |
| Amb Target | 24 | 90 | 126 | 24 | 42 | 66 | 90 | 126 | 168 |
| Non-Amb Range | 36-90 | 90-216 | 144-288 | 36-72 | 60-96 | 72-96 | 96-126 | 126-168 | 162-216 |
| Non-Amb Target | 66 | 162 | 216 | 66 | 78 | 84 | 114 | 150 | 192 |

In any of the aspects described herein, the therapy may comprise administering a fixed dose daily, on alternative days, on two consecutive days per week (e.g., weekends only), or for a period of time followed by a dosing reprieve of similar length (e.g., administering the fixed dose each day for ten days, not administering deflazacort for the following ten days, then optionally resuming administration). When dosing on alternative days, the deflazacort fixed dose would be about the same or about double (Two-Fold; 2×) the daily doses for the aspects described herein. For example, in one aspect, wherein the subject is aged 4-11 years and is ambulatory, and a fixed daily dose of 18 mg is selected, a dose of 36 mg would be selected for dosing on alternative days. When dosing two days per week, the deflazacort fixed dose would be about three to about ten times (e.g., six times, 6×) the daily doses described in the aspects provided herein. In one example, the subject is aged>11-18 years, weighs more than 75 kg and is non-ambulatory, a daily dose of 66-96 mg may be selected. In another example, the subject is aged 4-11 years, weighs more than or equal to 16 kg and less than 30 kg, and is ambulatory, a daily dose of 18 mg is selected. For the same dose taken twice weekly, dosing optionally is selected from 54-180 mg per administration (e.g., 114 mg per administration). When deflazacort is given for a period of time followed by a dosing reprieve of similar length, the dose would be similar to or up to three times higher than the daily doses in the aspects described. Any route of administration appropriate for deflazacort delivery is appropriate for use in the context of the invention, including oral or parenteral (e.g., intramuscular or intravenous) routes of administration.

In addition to providing fixed dose regimens for subjects based on age or weight class, the disclosure provides for improved regimens based on ambulatory status and CYP usage. Ambulatory status and CYP usage are described further below. Exemplary fixed dose regimens are provided in Table 1, which is provided merely to illustrate various aspects of the disclosure and is not meant to be limiting. In various aspects of the invention, subject classifications based on age or weight class are further stratified based on ambulatory status.

In another aspect, deflazacort therapy comprises, administering a fixed daily dose of deflazacort based on patient weight, ambulatory status and CYP inhibitor or inducer usage according to the regimen shown in Table 1a.

TABLE 1a

| Weight | Ambulatory/<br>CYP-Inhibitor/<br>CYP-Inducer<br>(mg/day) | Non-Ambulatory/<br>CYP-Inhibitor/<br>CYP-Inducer<br>(mg/day) |
| --- | --- | --- |
| ≤30 kg | 18/6/54-72 | 24/6-12/72-96 mg/day |
| 30 kg-≤50 kg | 36/12/108-144 mg/day | 42/6-12/126-168 mg/day |
| >50 kg | 48/12-18/144-192 mg/day | 54/18-24/162-216 mg/day |

In another aspect, deflazacort therapy comprises, administering a fixed daily dose of deflazacort based on patient weight and ambulatory status according to the regimen shown in Table 1b.

TABLE 1b

| Weight | Ambulatory | Non-Ambulatory |
| --- | --- | --- |
| ≤30 kg | 18 mg/day | 24 mg/day |
| >30 kg-≤50 kg | 36 mg/day | 42 mg/day |
| >50 kg | 48 mg/day | 54 mg/day |

In another aspect, Table 1c compares the weight based, standard-of-care (SOC) Current Dosing Table with a fixed dose deflazacort therapy.

TABLE 1c

| SOC<br>Weight<br>Range (kg) | SOC Total<br>Dose<br>(0.9 mg/kg/d) | SOC Total<br>Dose<br>(1.2 mg/kg/d) | Weight<br>(kg) | Amb<br>(mg/day) | Non-<br>Amb<br>(mg/day) |
| --- | --- | --- | --- | --- | --- |
| 20-21 | 18 | 24 | ≤30 | 18 | 24 |
| 22-24 | 21 | 28 | | | |
| 25-28 | 24 | 32 | | | |
| 29-31 | 27 | 36 | | | |
| 29-31 | 27 | 36 | >30-≤50 | 36 | 42 |
| 32-34 | 30 | 40 | | | |
| 35-38 | 33 | 44 | | | |
| 39-41 | 36 | 48 | | | |
| 42-44 | 39 | 52 | | | |
| 45-48 | 42 | 56 | | | |
| 49-51 | 45 | 60 | | | |
| 49-51 | 45 | 60 | >50 | 48 | 54 |
| 52-54 | 48 | 64 | | | |
| 55-58 | 51 | 68 | | | |
| 59-61 | 54 | 72 | | | |
| 62-64 | 57 | 76 | | | |
| 65-68 | 60 | 80 | | | |
| 69-71 | 63 | 84 | | | |
| 72-74 | 66 | 88 | | | |
| 75-78 | 69 | 92 | | | |
| 79-81 | 72 | 96 | | | |

TABLE 1c-continued

In this aspect, the rows in Table 1c that are shaded and repeated represent those narrow weight ranges in the Current Dosing Table where they bridge the broader fixed dose deflazacort therapy weight ranges. Based on the factors considered in the clinical simulations described herein, the differences in ambulatory status (wherein Amb represents an Ambulatory subject and Non-Amb represents a Non-Ambulatory subject, each at a dose in mg/day) show that a higher dose is recommended for a Non-Ambulatory subject compared to an Ambulatory subject. In one example comparing Table 1 and Table 1c, for an ambulatory subject having an age less than or equal to 11 years of age and a weight less than or equal to 16 kg, Table 1 suggests an Ambulatory Range (Amb Range) dose of from 6 to 18 mg/day, which is lower than the Table 1 Exemplary Dose of from 6 to 36 mg/day, not covered in the Table 1c Current Dosing Table and inclusive (at the higher end) of the claimed fixed dose therapy. The result of clinical trial simulations shown in FIG. 6 and exemplified in FIG. 17, however, predict that the lower dose for the Table 1 Ambulatory Range will be, in the long term, an efficacious therapeutic dose while reducing the amount of adverse events compared to the 0.9 mg/kg/day dose of the Current Dosing Table and retaining muscle strength longer compared to the 1.2 mg/kg/day dose of the Current Dosing Table. Table 1c shows that the fixed dose therapy provides a single, comparatively lower daily dose, replacing the SOC total dose for both the 0.9 mg/kg/day and 1.2 mg/kg/day doses with a less complicated regimen that addresses the effect of ambulatory status and other factors while maintaining efficacy and enhancing safety.

In other words, while the dose ranges in Table 1 for the age, weight, ambulation and CYP classes are based on the simulations, they are all expected long-term to mitigate under-dosing and provide higher doses for non-ambulatory subjects while balancing safety issues compared to the Current Dosing Chart shown in Table 1c. It is to be understood by those skilled in the art that the fixed doses compared in Table 1c with the Current Dosing Table represent only one example of therapeutic ranges determined by the clinical simulations to balance long-term efficacy and safety. It is also to be understood that the fixed doses exemplified in Table 1c are considered optimal in comparison to the Current Dosing Chart because they are based on the optimal three (3) Weight Group simulation results discussed herein.

For oral administration, deflazacort is, optionally, formulated as a tablet or an oral suspension. Deflazacort tablets are supplied at 6 mg, 18 mg, 30 mg or 36 mg strength tablets. Additional components of a tablet may include, for instance, colloidal silicon dioxide, lactose monohydrate, magnesium stearate, and pre-gelatinized corn starch. Deflazacort oral suspension is supplied at 22.75 mg/mL, as 13 mL in a 20 mL bottle. An oral suspension may comprise, for example, acetic acid, aluminum magnesium silicate, benzyl alcohol, carboxymethylcellulose sodium, polysorbate 80, purified water, and sorbitol. One of ordinary skill will appreciate that these are merely examples of excipients and inactive components suitable for oral administration, and additional or alternative formulations may be used.

In one aspect, the pharmaceutical composition for use in providing a fixed dose deflazacort therapy to a subject that is suffering from Duchenne muscular dystrophy (DMD) comprises, oral administration of the composition formulated as an oral dosage form selected from a tablet or an oral suspension.

In another aspect, the tablet contains an amount of deflazacort selected from 6 mg, 18 mg, 30 mg or 36 mg in admixture with excipients selected from colloidal silicon dioxide, lactose monohydrate, magnesium stearate, and pregelatinized corn starch.

In another aspect, the oral suspension contains 22.75 mg/mL of deflazacort in a suspension with acetic acid, aluminum magnesium silicate, benzyl alcohol, carboxymethylcellulose sodium, polysorbate 80, purified water, and sorbitol.

In another aspect, the deflazacort oral suspension contains 13 mL of the suspension in a 20 mL bottle.

Clinical Trial Pharmacokinetic Analysis/Exposure Simulations

Pharmacokinetic analysis was performed as part of an open label, Phase 1 single-period study. Twenty-six (26) male DMD subjects were enrolled, consisting of children (ages 4 up to 12) and adolescents (ages 12 to 16, inclusive) with at least 12 subjects between the ages of 4 and 12 (children). The primary objective of the study was characterization of the single-dose and steady-state PK of deflazacort and its active deflazacort metabolite (21-desDFZ). The characterization of the PK of the 21-desDFZ metabolite 6β-OH-21-desDFZ was included as a secondary outcome. A total of 24 subjects (16 children and 8 adolescents) received deflazacort tablets (0.9 mg/kg/day) for 8 days. Blood samples for PK profiles were collected on Days 1 and 8. All 24 subjects who completed the study had sufficient data to use in the PK analysis. Plasma 21-desDFZ concentrations were quantifiable by the time of the first post-dose sample collection (0.5 hours) in all children and adolescents on Days 1 and 8. Plasma 21-desDFZ concentrations remained above the limit of quantification in most subjects over the 8-hour sampling window on both study days.

On Days 1 and 8, 21-desDFZ exposure parameters were slightly higher for adolescents compared to children (data not shown). However, the geometric mean Cmax for adolescents was almost double that in children on Day 1 and 1.5 fold that in children on Day 8 (FIG. 1). Moreover, the geometric mean AUClast and AUCinf values in adolescents were roughly 1.5- to 1.6-Fold that in children on Days 1 and 8. The geometric mean terminal elimination half-life values were also similar between study populations at 1.17 hours in children and 1.34 hours in adolescents on Day 1.

There was a trend toward increasing exposure (Cmax, AUClast, and AUCinf, or AUCtau) with increasing age; however, the child plasma concentration was consistently below the norm compared to the adolescent plasma concentration (FIG. 5). This pharmacokinetic trend was better explained as a function of dose received rather than age alone (FIG. 5). The dose normalized exposure parameters (FIG. 4) and the dose dependent parameters: clearance (FIG. 2) and volume of distribution (FIG. 4), though, were consistent between children and adolescents.

Plasma 6β-OH-21-desDFZ (primary, inactive metabolite of 21-desDFZ) concentrations were quantifiable by the time of the first post-dose sample collection (0.5 hours) in all children and adolescents on Days 1 and 8. Plasma 6β-OH-21-desDFZ concentrations remained above the limit of quantification in most subjects over the 8-hour sampling window on both sampling days. On Days 1 and 8, 6β-OH-21-desDFZ exposure parameters were slightly higher for adolescents compared to children. The geometric mean Cmax for adolescents was roughly 1.25-Fold that in children on Day 1 and 1.30-Fold that in children on Day 8. Geometric mean AUClast and AUCinf values in adolescents were roughly 1.25-Fold that in children on Days 1 and 8. The geometric mean terminal elimination half-life values were also similar between study populations at 1.63 hours in children and 1.72 hours in adolescents on Day 1.

Figure 2:
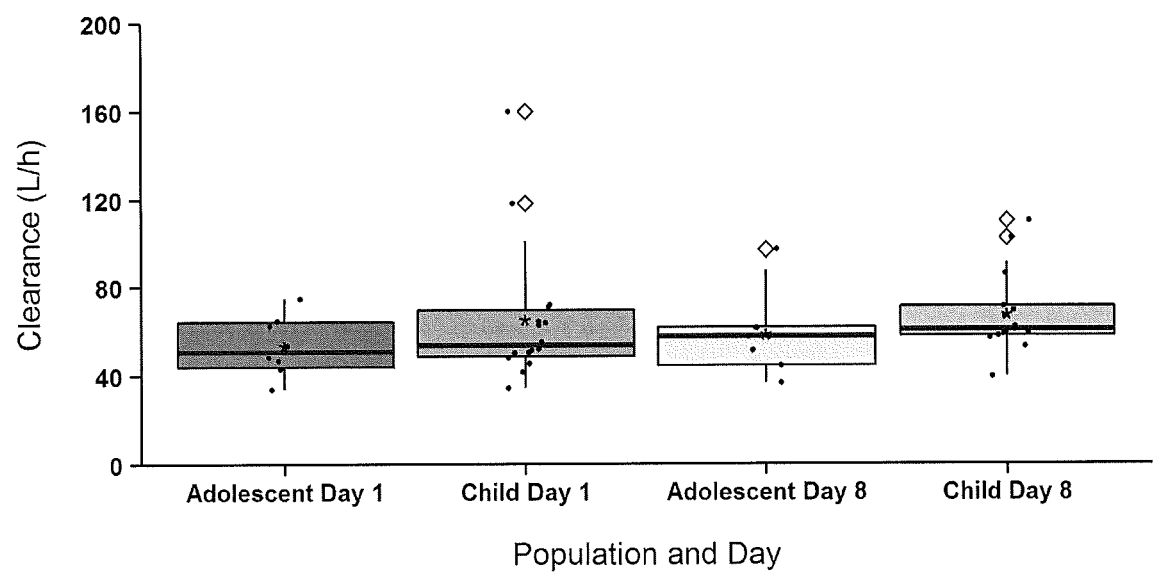
FIG. 2 is a boxplot comparing 21-desDFZ clearance (CL/F and CLss/F) by day and study population with individual values included (linear scale). There were no differences in the clearance values (CL/F) of 21-desDFZ calculated after a single oral dose of deflazacort and at steady-state between children and adolescents.
Figure 3:
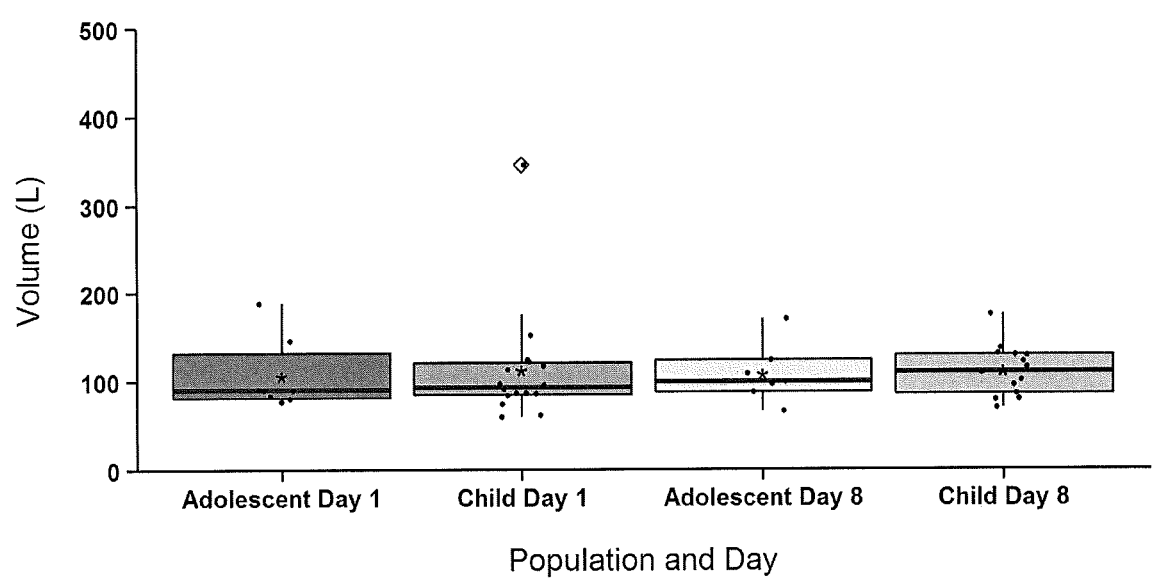
FIG. 3 is a boxplot comparing 21-desDFZ volume of distribution (Vz/F and Vzss/F) by day and study population with individual values included (linear scale). There were no differences in the volume of distribution (Vd/F) of 21-desDFZ calculated after a single oral dose of deflazacort and at steady-state between children and adolescents.

Children and adolescents in the study were administered the same doses for 7 days, 0.9 mg/kg/day; however, the exposures to 21-desDFZ after administration of deflazacort on Days 1 and 8 were markedly decreased in children compared to adolescents (See FIG. 1 for Day 8 plasma concentration-time curves, Day 1 data not shown). However, these differences were more a function of total dose received (FIG. 4) rather than differences between patient populations as the dose-dependent parameters, CL and Vd were similar between children and adolescents (FIGS. 2 and 3). Simulated plasma exposures to 21-desDFZ after a 0.9 mg/kg/day dose of deflazacort and a 1.2 mg/kg/day dose of deflazacort resulted in nearly equivalent plasma exposures (FIG. 6). The pharmacokinetic data from this patient population showed that the youngest patients are at risk for the greatest variance in total dose administered in relation to the target, weight-based dose of 0.9 mg/kg/day. Review of the total doses of deflazacort administered to the youngest children with DMD (of lowest weight) demonstrated a considerable number of patients were under-dosed. The clinical pharmacokinetic data of 21-desDFZ after oral administration of deflazacort showed that children clear 21-desDFZ to the same extent as adolescents and similar to adults (FIGS. 1-5).

These data support the use of a simplified, fixed-dose regimen to more appropriately administer a deflazacort therapy to subjects with DMD, particularly subjects 11 years of age and younger. Based on the properties of deflazacort within the child and adolescent populations, a simplified, fixed dose regimen provides more appropriate exposures of the active 21-desDFZ deflazacort metabolite across age groups.

Clinical Trial Simulations

Exposure-response clinical trial simulations, modeling both efficacy and safety endpoints, were employed to identify fixed dose regimens of deflazacort treatment to children and adolescents with DMD to maximize exposure to the active metabolite and manage potential adverse side effects.

Figure 7:
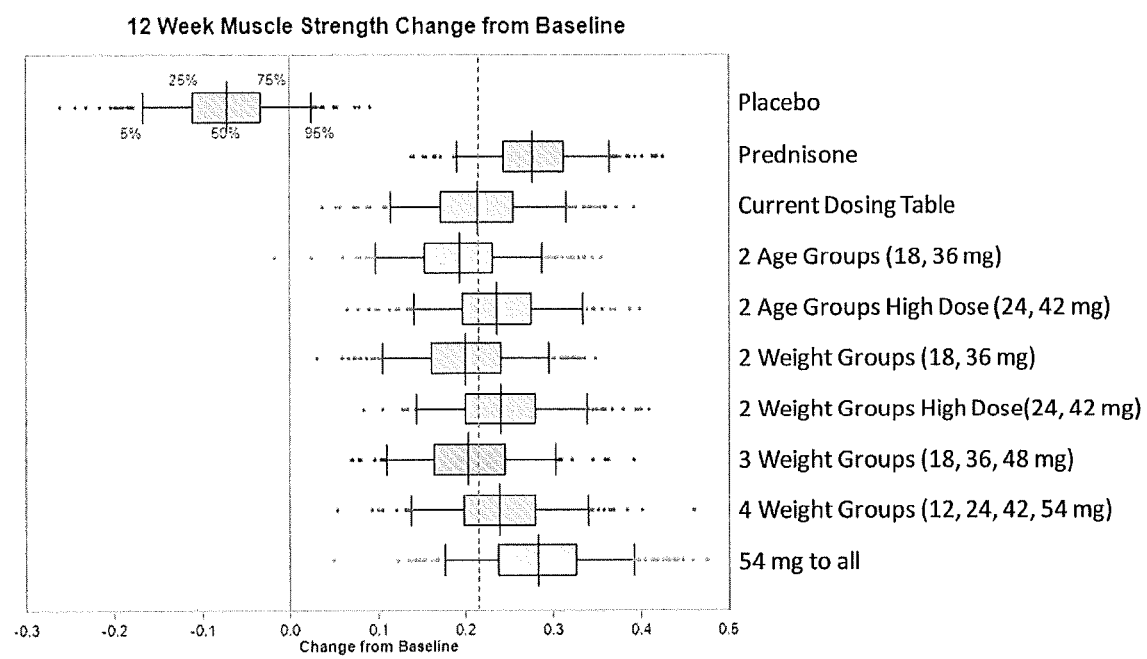
FIG. 7 is a box plot showing the Week 12 change in muscle strength by various fixed-dose regimen treatment arms, assuming 50 subjects per arm with doses not dependent on ambulatory status after 10,000 clinical trial simulations. The box represents the 25th and 75th percentiles, with the median, while the 5th and 95th percentiles are depicted by a thin line and outliers are represented by dots. The vertical dotted line represents the median results using the Current Dosing Table (0.9 mg/kg). The treatment arms are given in the following order: placebo, prednisone, Current Dosing Table, two (2) Age groups, two (2) Age groups High Dose, two (2) Weight groups, two (2) Weight groups High Dose, three (3) Weight groups, four (4) Weight groups, and 54 mg to all.
Figure 8:
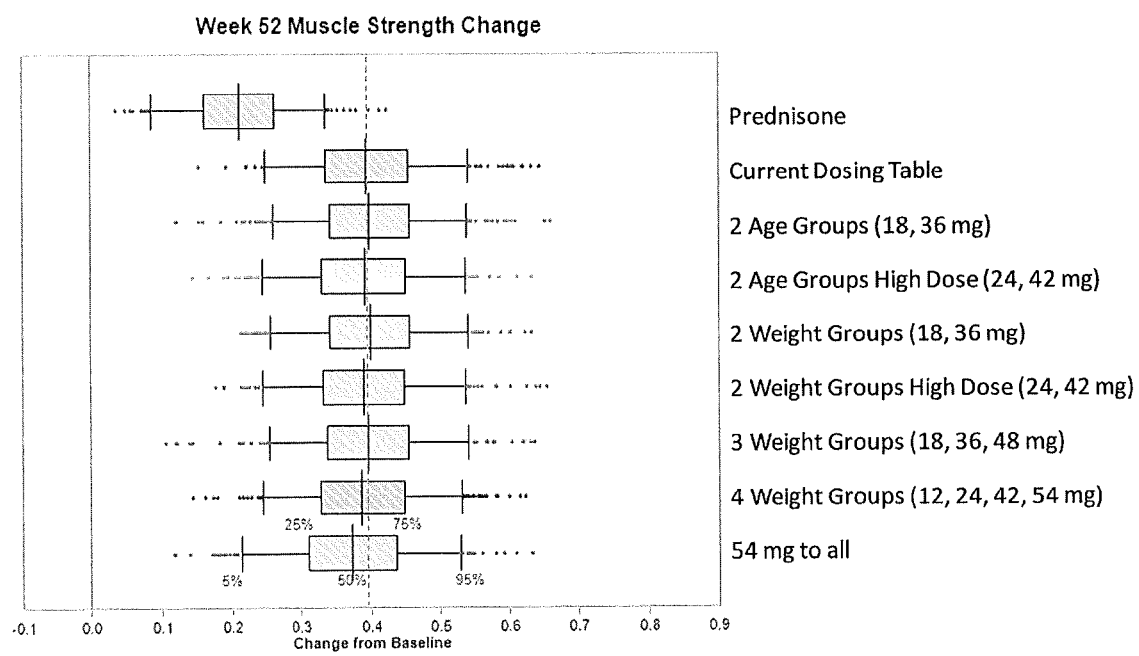
FIG. 8 is a box plot showing the Week 52 change in muscle strength by various fixed dose regimen treatment arms, assuming 50 subjects per arm with doses not dependent on ambulatory status after 10,000 clinical trial simulations. The box represents the 25th and 75th percentiles, with the median, while the 5th and 95th percentiles are depicted by a thin line and outliers are represented by dots. The vertical dotted line represents the median results using the Current Dosing Table. The treatment arms are given in the following order: prednisone, Current Dosing Table, two (2) Age groups, two (2) Age groups High Dose, two (2) Weight groups, two (2) Weight groups High Dose, three (3) Weight groups, four (4) Weight groups, and 54 mg to all.
Figure 9:
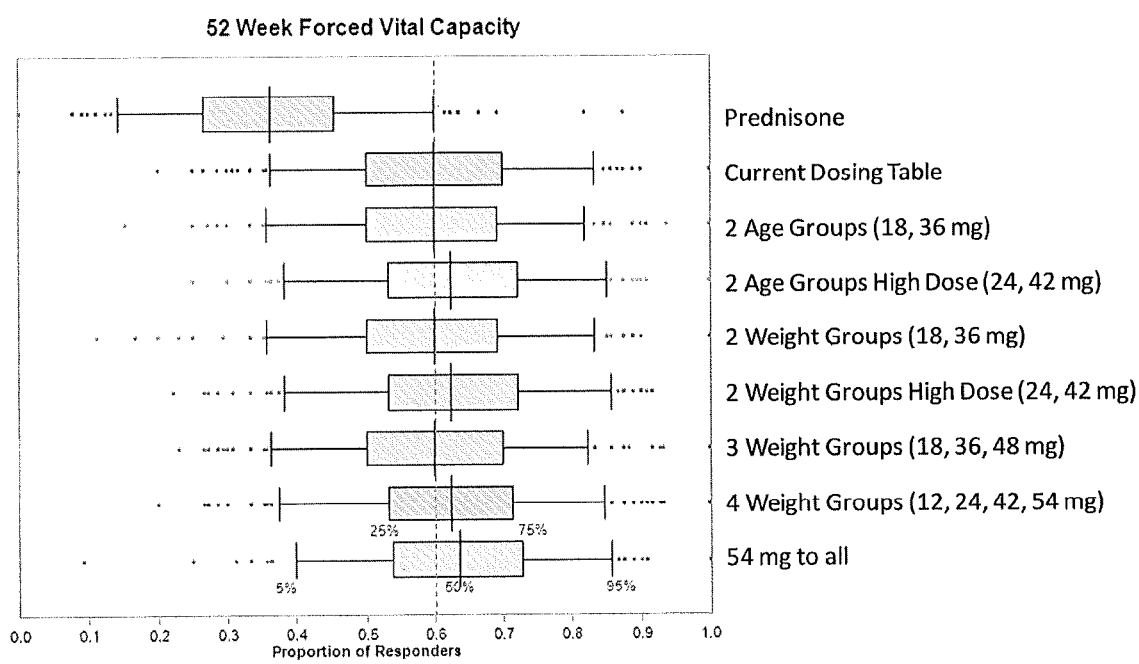
FIG. 9 is a box plot showing the Week 52 Non-ambulatory FVC (Forced Vital Capacity) by Responders by various fixed-dose treatment arms, assuming 50 subjects per arm after 10,000 clinical trial simulations with doses not dependent on ambulatory status. The box represents the 25th and 75th percentiles, with the median, while the 5th and 95th percentiles are depicted by a thin line and outliers are represented by dots. The vertical dotted line represents the median results using the Current Dosing Table. The treatment arms are given in the following order: prednisone, Current Dosing Table, two (2) Age groups, two (2) Age groups High Dose, two (2) Weight groups, two (2) Weight groups High Dose, three (3) Weight groups, four (4) Weight groups, and 54 mg to all.
Figure 10:
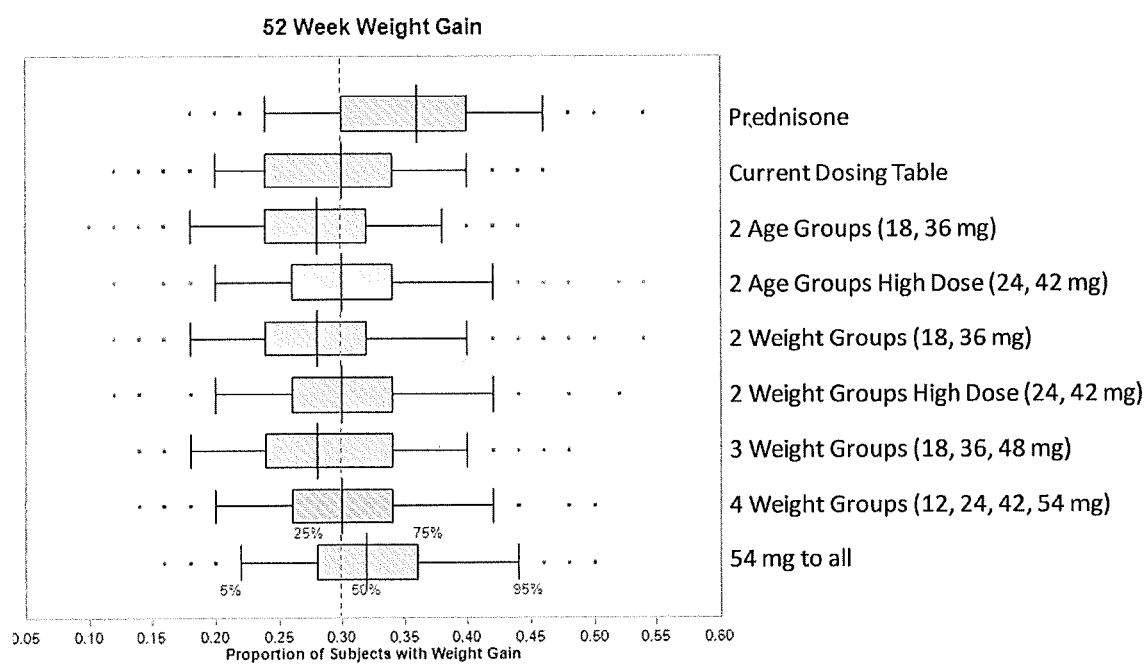
FIG. 10 is a box plot showing the Week 52 Proportion of Subjects with Weight Gain by various fixed-dose treatment arms, assuming 50 subjects per arm after 10,000 clinical trial simulations with doses not dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: prednisone, Current Dosing Table, two (2) Age groups, two (2) Age groups High Dose, two (2) Weight groups, two (2) Weight groups High Dose, three (3) Weight groups, four (4) Weight groups, and 54 mg to all.
Figure 11:
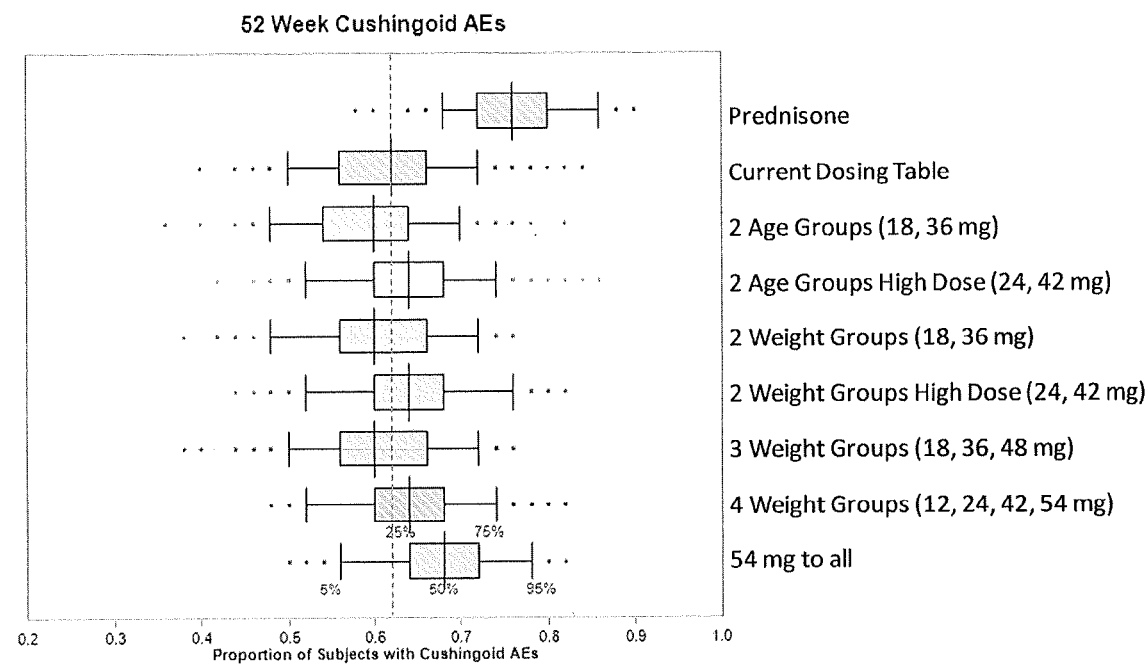
FIG. 11 is a box plot showing the Week 52 Proportion of Subjects with Cushingoid Syndrome by various fixed-dose treatment arms, assuming 50 subjects per arm after 10,000 clinical trial simulations with doses not dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: prednisone, Current Dosing Table, two (2) Age groups, two (2) Age groups High Dose, two (2) Weight groups, two (2) Weight groups High Dose, three (3) Weight groups, four (4) Weight groups, and 54 mg to all.
Figure 12:
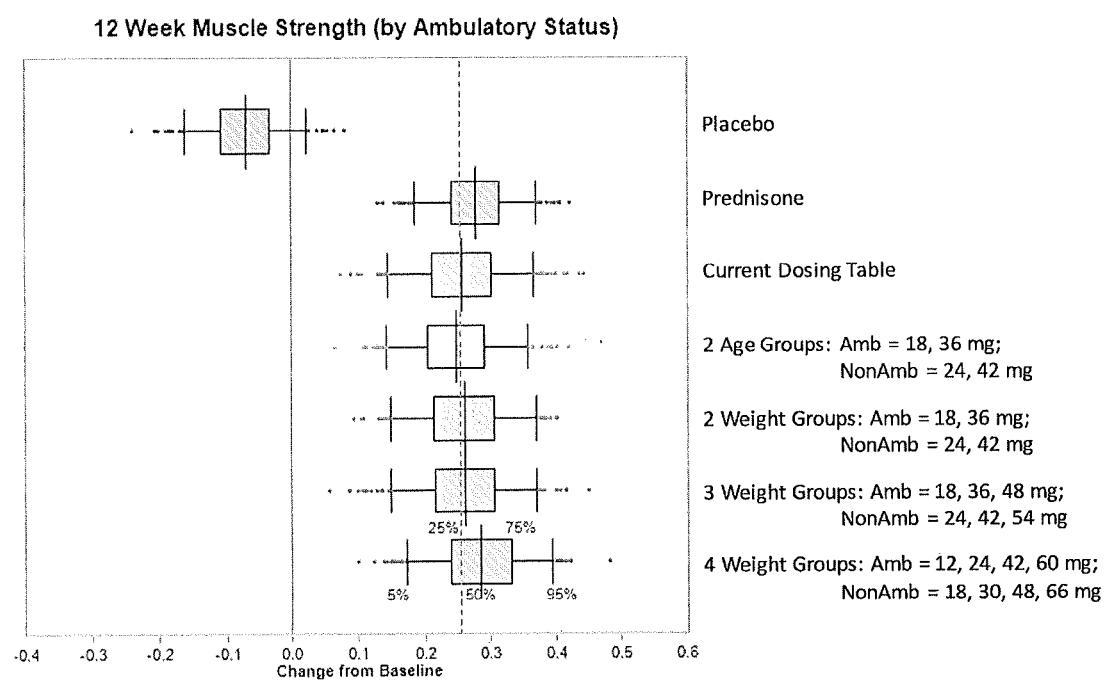
FIG. 12 is a box plot showing the Week 12 change in muscle strength by various fixed-dose treatment arms, assuming 50 subjects per arm after 10,000 clinical trial simulations with doses dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: placebo, prednisone, Current Dosing Table, two (2) Age groups (Amb and Non-Amb), two (2) Weight groups (Amb and Non-Amb), three (3) Weight groups (Amb and Non-Amb), and four (4) Weight groups (Amb and Non-Amb).
Figure 13:
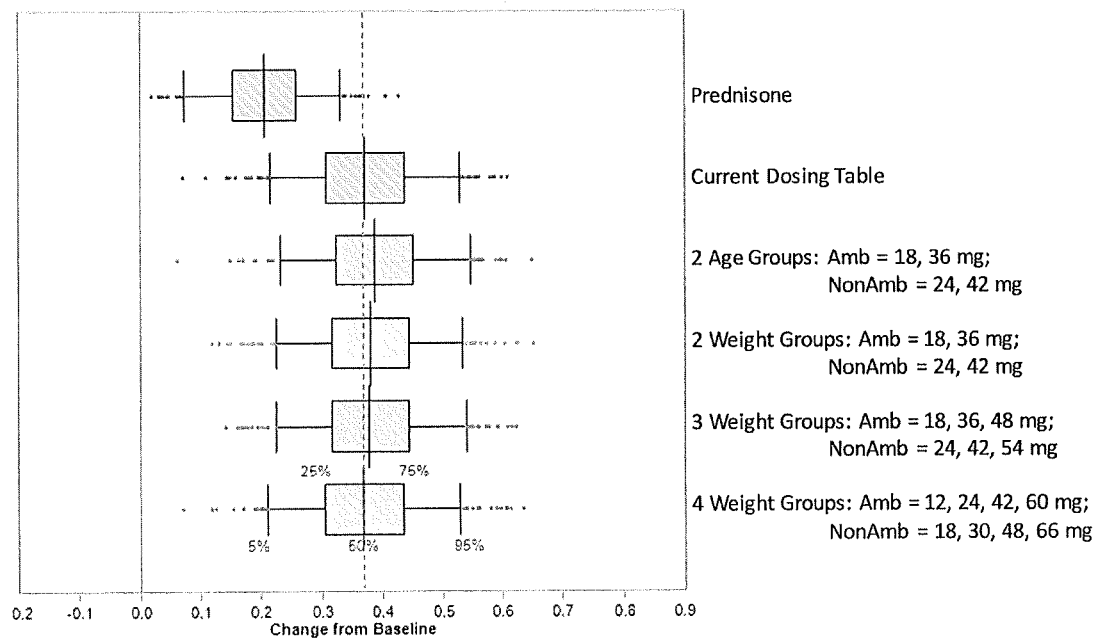
FIG. 13 is a box plot showing the Week 52 change in muscle strength by various fixed-dose treatment arms, assuming 50 subjects per arm after 10,000 clinical trial simulations with doses dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: Prednisone, Current Dosing Table, two (2) Age groups (Amb and Non-Amb), two (2) Weight groups (Amb and Non-Amb), three (3) Weight groups (Amb and Non-Amb), and four (4) Weight groups (Amb and Non-Amb).
Figure 14:
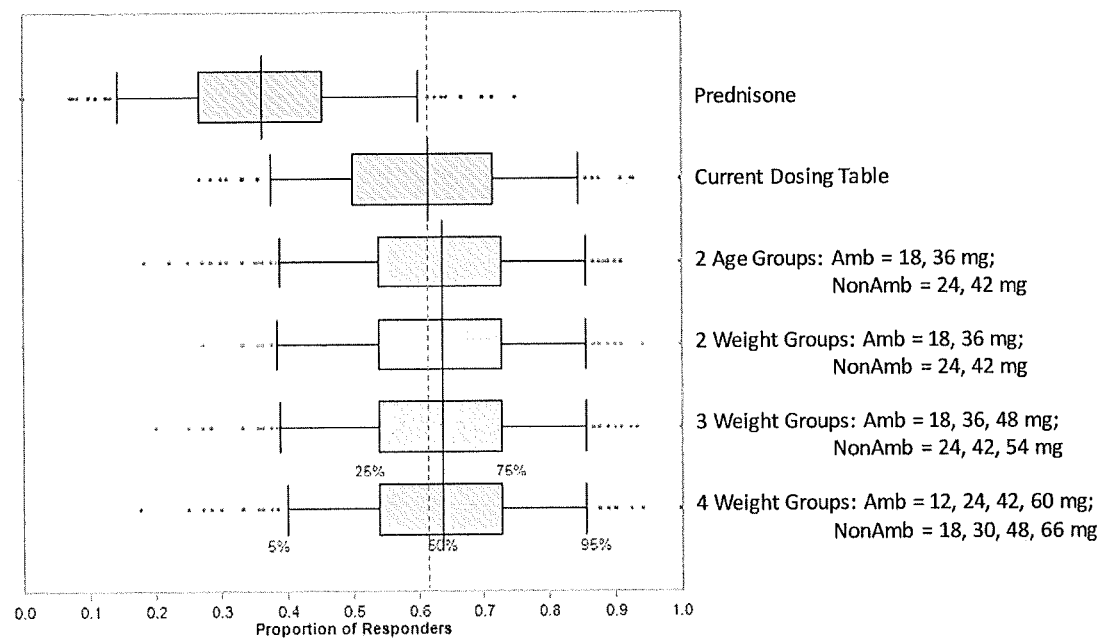
FIG. 14 is a box plot showing the Week 52 FVC Responders by various fixed-dose treatment arms, assuming 50 subjects per arm with after 10,000 clinical trial simulations doses dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: prednisone, Current Dosing Table, two (2) Age groups (Amb and Non-Amb), two (2) Weight groups (Amb and Non-Amb), three (3) Weight groups (Amb and Non-Amb), and four (4) Weight groups (Amb and Non-Amb).
Figure 15:
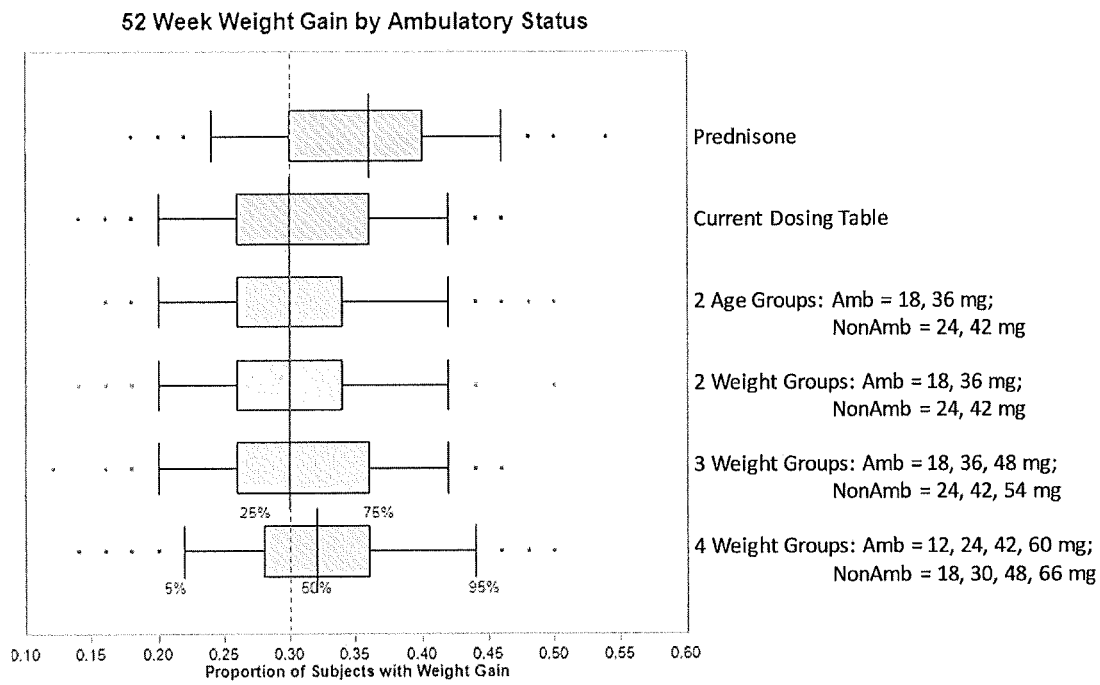
FIG. 15 is a box plot showing the Week 52 Proportion of Subjects with Weight Gain by various fixed-dose treatment arms, assuming 50 subjects per arm after 10,000 clinical trial simulations with doses dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: prednisone, Current Dosing Table, two (2) Age groups, two (2) Weight groups (Amb and Non-Amb), three (3) Weight groups (Amb and Non-Amb), and four (4) Weight groups (Amb and Non-Amb).
Figure 16:
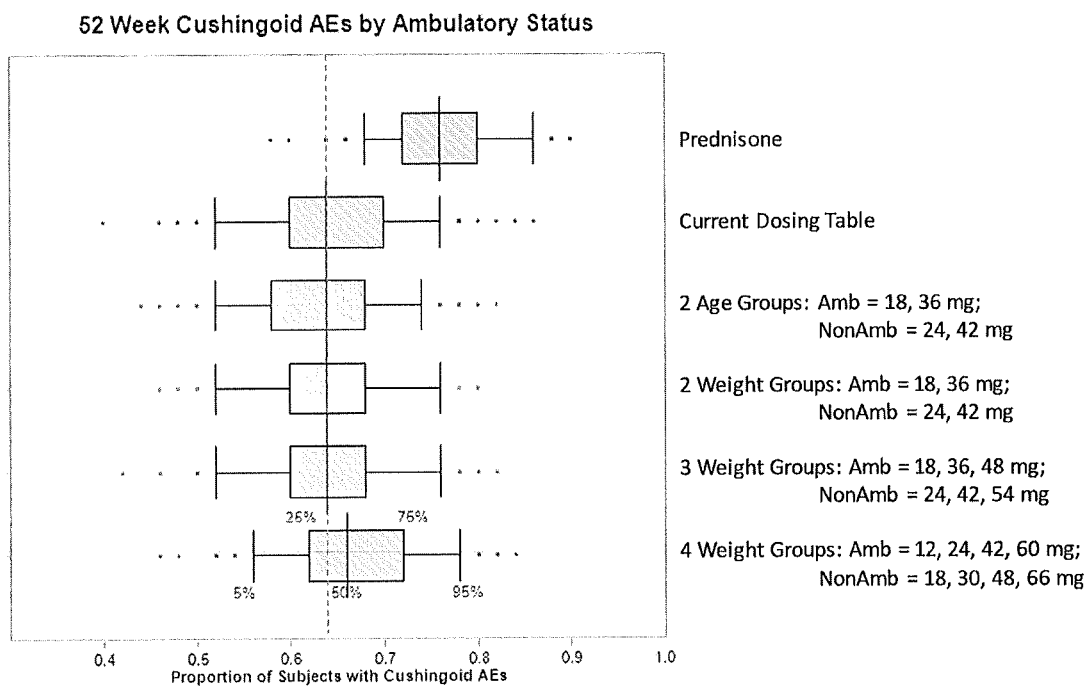
FIG. 16 is a box plot showing the Week 52 Proportion of Subjects with Cushingoid Syndrome by various fixed-dose treatment arms, assuming 50 subjects per arm after 10,000 clinical trial simulations with doses not dependent on ambulatory status. The box represents the 25th and 75th percentiles, with the median, while the 5th and 95th percentiles are given with the thin line and outliers are represented by dots. The vertical dotted line represents the median results using the Current Dosing Table. The treatment arms are given in the following order: prednisone, Current Dosing Table, two (2) Age groups (Amb and Non-Amb), two (2) Weight groups (Amb and Non-Amb), three (3) Weight groups (Amb and Non-Amb), and four (4) Weight groups (Amb and Non-Amb).

First, for each subject, a random sample was taken from the Dose-normalized AUC from a clinical trial and multiplied by a random sample of the body weight from the CDC height and weight charts for children and by the dosing regimen proposed (e.g., Current Dosing Table or each fixed dose). Second, depending on the AUC, the subject was assumed to have efficacy and safety similar to deflazacort 0.9 mg/kg, deflazacort 1.2 mg/kg, or placebo as illustrated in FIG. 6. Third, each subject was given values for the change in muscle strength at 12 or 52 weeks (FIG. 7 and FIG. 8, respectively), and allocated as a non-ambulatory FVC responder at 52 weeks (yes/no) (FIG. 9), experiencing weight gain at 52 weeks (yes/no) (FIG. 10), and experiencing Cushingoid Syndrome at 52 weeks (yes/no) (FIG. 11). This was achieved by randomly selecting from distributions (developed from previous study results plus uncertainty). Fourth, steps 1-3 were conducted assuming 50 subjects/arm for placebo, prednisone and 10 different fixed-dose schemes of deflazacort. Fifth, 10,000 clinical trials were simulated, and safety and efficacy were summarized.

The dosing regimens shown in FIGS. 7-16 were simulated according to the clinical trial treatment arm classifications: Placebo, Prednisone, Current Dosing Table, Age Group Dosing, Weight Group Dosing, Combined Ambulatory Status and Age Group Dosing, Combined Ambulatory Status and Weight Group Dosing and Positive Control High Dosing, where simulated data in each Figure shows results as follows according to the groupings:

[A] Current Dosing Table currently used to approximate 0.9 mg/kg;

[B] Dosing based on age groups:
  Two (2) Age Groups (Lower Doses): ≤11 yr=18 mg, >11 yr=36 mg;
  Two (2) Age Groups (Higher Doses): ≤11 yr=24 mg, >11yr=42 mg;

[C] Dosing based on weight groups:
  Two (2) Weight Groups (Lower Doses): ≤30 kg=18 mg, >30 kg=36 mg;
  Two (2) Weight Groups (Higher Doses): ≤30 kg=24 mg, >30 kg=42 mg;
  Three (3) Weight Groups: ≤30 kg=18 mg, 30-≤50 kg=36 mg, >50 kg=48 mg;
  Four (4) Weight Groups: ≤16 kg=12 mg, 16-≤30 kg=24, 30-≤50 kg=42, >50 kg=54 mg;

[D] Dosing based on ambulatory status (Amb or Non-Amb) and two (2) Age Groups:
  Amb & ≤11 yr=18 mg,
  Amb & >11 yr=36 mg,
  Non-Amb & ≤11 yr=24 mg,
  Non-Amb & ≤11 yr=42 mg;

[E] Dosing based on ambulatory status (Amb or Non-Amb) and two to four (2-4) Weight Groups:
  Two (2) Weight Groups:
    Amb & ≤30 kg=18 mg,
    Amb & >30 kg=36 mg;
    Non-Amb & ≤30 kg=24 mg,
    Non-Amb & >30 kg=42 mg;
  Three (3) Weight Groups:
    Amb & ≤30 kg=18 mg,
    Amb & 30-≤50 kg=36 mg,
    Amb & >50 kg=48 mg;
    Non-Amb & ≤30 kg=24 mg,
    Non-Amb & 30-≤50 kg=42 mg,
    Non-Amb & >50 kg=54 mg;
  Four (4) Weight Groups:
    Amb & ≤16 kg=12 mg,
    Amb & 16-≤30 kg=24 mg,
    Amb & 30-≤50 kg=42 mg,
    Amb & >50 kg=60 mg;
    Non-Amb & ≤16 kg=18 mg,
    Non-Amb & 16-≤30=30 mg,
    Non-Amb & 30-≤50 kg=48 mg,
    Non-Amb & >50 kg=66 mg.

The overall results for dosing regimens not related to ambulatory status are described in FIG. 17 and illustrated in FIGS. 7-11. In general, most dosing regimens yield similar changes in muscle strength, FVC, weight gain, and Cushingoid Syndrome. While still acceptable in certain aspects, there may be a loss of efficacy with two (2) Age Groups (Lower Doses) and two (2) Weight Groups (Lower Doses) (for both muscle strength and FVC) and an increase in the incidence of weight gain and Cushingoid Syndrome with two (2) Age Groups (Higher Doses), two (2) Weight Groups (Higher Doses), and four (4) Weight Groups.

As shown in FIG. 17, clinical trial simulation results (n=10,000) of the control arms and the recommended simplified dosing regimen using the overall DMD population are presented. It is important to note that there were only very small differences seen among the various simplified dosing regimens. Simulations replicating results from the pivotal Griggs study showed that 1.2 mg/kg/day SOC dose regimen had a greater average change in muscle strength than the 0.9 mg/kg/day SOC dose regimen at 12 weeks (0.310 vs 0.185, respectively), a slightly greater proportion of FVC responders at 52 week (0.636 vs 0.626, respectively), but a slightly lower average change in muscle strength at 52 weeks (0.369 vs 0.424, respectively). The proportion of subjects with weight gain or Cushingoid Syndrome adverse events (AEs) was higher for the 1.2 mg/kg/day dose group than the 0.9 mg/kg/day dose group at 52 weeks (weight gain: 0.328 vs 0.286, respectively, and Cushingoid Syndrome AEs: 0.687 vs 0.600, respectively). Because all of the deflazacort dosing simulations were randomly sampled from these distributions, these values define the range of the deflazacort simulation results for each simplified dosing regimen. Placebo data was only available for the 12-week change in muscle strength, and as expected, the results showed a slight decline in muscle strength (average change of −0.072). Efficacy predictions for prednisone ranked it much lower than the deflazacort 0.9 mg/kg/day for the 52 week change in muscle strength (mean change of 0.212 and 0.424 for prednisone and deflazacort 0.9 mg/kg/day, respectively) and FVC responders (response rate of 0.365 and 0.626, respectively), but higher than the 0.9 mg/kg/d deflazacort for 12-week change in muscle strength (mean change of 0.278 and 0.185, respectively). Prednisone was also predicted to have a higher proportion of subjects with weight gain or Cushingoid Syndrome AEs than deflazacort 0.9 mg/kg/day.

FIG. 17 shows that results from the clinical trial simulations using the Current Dosing Table were within the ranges defined by the replicated results from the deflazacort 0.9 mg/kg/day SOC dose regimen, but were slightly lower for the average 52 week change in muscle strength (0.396 and 0.424 for the fixed dose regimen and 0.9 mg/kg/day for the SOC regimen, respectively) and the 52 week FVC responders (0.600 and 0.626, respectively). The results of the positive control (54 mg deflazacort to all subjects) predicted higher 12-week change in muscle strength and FVC responders, but both regimens predicted a higher proportion of subjects with AEs. These results indicate the clinical trial simulation methodology (including assumptions) was functioning as expected. The simplified dosing regimen (not taking ambulatory status into account) that optimally balanced efficacy and safety was based on dosing deflazacort using the three (3) Weight Groups (≤30 kg=18 mg, >30≤50 kg=36 mg, >50 kg=48 mg) regimen. This regimen predicted slightly less (4%) efficacy to the Current Dosing Table (0.205 vs 0.214) for 12 week change in muscle strength, but comparable efficacy at 52 weeks (0.397 vs 0.396) for 52 week change in muscle strength, and 0.598 vs 0.600 for FVC responders, respectively), while predicting comparable or slightly lower AEs (0.290 vs 0.293 for weight gain, and 0.607 vs 0.613 for Cushingoid Syndrome AEs, respectively). Comparing this dosing regimen with replicated results from the SOC deflazacort 0.9 mg/kg/day and deflazacort 1.2 mg/kg/day dosing regimen suggests that the proportion of subjects with weight gain or Cushingoid Syndrome AEs would be comparable to deflazacort 0.9 mg/kg/day (within 1%) while producing changes in muscle strength better than deflazacort 1.2 mg/kg/day at 12 weeks, but slightly (about 6-7%) less than 0.9 mg/kg/day at 52 weeks and slightly (<6%) lower FVC responder rates.

The results for dosing regimens which are dependent on ambulatory status are described in FIG. 18 and illustrated in FIGS. 12-16. In general, most dosing regimens yield similar changes in muscle strength, FVC, weight gain, and Cushingoid Syndrome. Four (4) Weight Groups by ambulatory status resulted in greater efficacy and greater incidence of weight gain or Cushingoid Syndrome.

Simulation results of the control arms and the recommended simplified dosing regimens for the DMD population stratified by ambulation status are shown in FIG. 18. Once again, there were only very small differences seen among the various dosing regimens. Because clinical trial simulations stratified by ambulatory status randomly sampled efficacy and safety results and weight distributions from simulations based on ambulatory status, the absolute values of the endpoints in FIG. 18 for the simulated clinical trial arms (Current Dosing Table, Placebo and prednisone) are different from those described in FIG. 17. Therefore, the simplified fixed dose regimen simulations by ambulatory status should only be interpreted relative to the Current Dosing Table shown in Table 1c. Results of the clinical trial simulations stratified by ambulatory status revealed that using simplified dosing regimens based on ambulatory status and two (2) Weight Groups, or three (3) Weight Groups both yielded comparable results to each other and the Current DFZ Dosing Table.

Conclusions from Clinical Trial Pharmacokinetic Analysis/Exposure Simulations

Clinical trial simulations were conducted to assess whether a simplified fixed dose deflazacort regimen would produce comparable safety and efficacy to the Current Dosing Table as well as comparable results from Phase 3 studies using the SOC 0.9 mg/kg/day regimen in pediatric patients with DMD. The concepts from the FDA's Exposure-Response Guidance (2003) were used in the analyses. There have been numerous examples where modeling and simulation have led to approved doses not studied in a Phase 3 clinical study, including: pasireotide in Cushings' disease (Yu 2016), mirabegron in the treatment of overactive bladder (Huang 2013, Astellas 2015) and clevidipine in the treatment of hypertension (Lee 2011), among others. Because both exposure and response were not available in the same subjects receiving deflazacort, the clinical trial simulations show how utilizing safety and efficacy data from pivotal studies can be linked to dose normalized PK data to predict safety and efficacy outcomes for a simplified fixed dose regimen.

The first important finding from the analysis was that there was substantial overlap in the predicted 21-desDFZ AUC following administration of deflazacort 0.9 mg/kg/day and 1.2 mg/kg/day (FIG. 6). This large overlap between doses is the fundamental reason for similar efficacy and safety results from clinical trial simulations of numerous dosing paradigms, with only minor differences predicted between regimens actually used. Therefore, there is no real clinical need for an extensive dosing table (as exemplified by the Current Dosing Table) to target deflazacort 0.9 mg/kg/day, which may introduce errors in dosing because of its complexity.

To determine the optimal simplified dosing regimen, a number of simplified dosing regimens describe herein were assessed. Whether or not ambulatory status was taken into account, the results of the simulations honed in on a simplified dosing regimen using three (3) weight groups to provide an optimal balance of efficacy and safety comparable to the results using the Current Dosing Table. While the results for the dosing regimen based on ambulatory status and two (2) weight groups (Amb & ≤30 kg=18 mg, Non-Amb & ≤30 kg=24 mg, Amb & >30 kg=36 mg, Non-Amb & >30 kg=42 mg) were very similar to the dosing regimen based on ambulatory status and three (3) weight groups, use of the three (3) weight groups better accounts for the fact that DMD patients are more likely to live into adulthood and require continued treatment. With regards to doses administered to non-ambulatory subjects, the current clinical practice maintains or reduces the deflazacort dose to patients after they become non-ambulatory. However, these simulations show that modestly increasing the dose administered to non-ambulatory patients is likely to increase efficacy (muscle strength and/or pulmonary function). Thus, the clinical trial simulations suggest that a change in clinical practice of dosing deflazacort to non-ambulatory patients should be considered.

Another important finding of the clinical trial simulations is that a simplified dosing regimen using three (3) Weight Groups are predicted to have a lower probability of exceeding the exposures simulated for clinical use than dosing according to the Current Dosing Table (7.91% vs 11.4% not accounting for ambulatory status; 11.5% vs 16.1% by ambulatory status). This finding suggests that simplifying the dosing regimen is unlikely to result in differences in safety compared to the Current Dosing Table. Thus, like the examples of mirabegron (Huang 2013; Astellas 2015), clevidipine (Lee 2011) and pasireotide (Yu 2016), modeling and simulation has identified more reasonable dosing regimens that improve the benefit/risk profile of deflazacort, without exposing subjects to higher exposures of deflazacort and increased risk. Accordingly, the clinical trial simulation data described herein demonstrate that a fixed-dose regimen (mg/day) based on three (3) weight groups and consideration of ambulatory status to provide a more consistent, simplified deflazacort dosing regimen than the Current Dosing Table.

CYP3A Inducers and Inhibitors

This disclosure further provides a deflazacort therapy comprising, administering to a subject in need thereof a therapeutically effective amount of deflazacort and avoiding administration of an inducer or inhibitor of cytochrome P450 3A (CYP3A), such as CYP3A4 (EC 1.14.13.97). The cytochrome P450 family of proteins comprises monooxygenases involved in drug metabolism and synthesis of biomolecules. In various aspects, the CYP3A4 inducer may be a moderate or strong CYP3A4 inducer. For CYP enzymes, the FDA generally defines a "strong inducer" as one that caused a ≥80% decrease in plasma AUC in clinical evaluations. Examples of strong inducers identified by the FDA include, e.g., avasimibe, carbamazepine, phenytoin, rifampin, and St. John's wort. U.S. Food and Drug Administration, Development and Drug Interactions: Table of Substrates, Inhibitors and Inducers, available at www.fda.gov/Drugs/DevelopmentApprovalProcess/DevelopmentResources/DrugInteractionsLabeling/ucm093664.htm. The FDA generally defines a "moderate inducer" as one that caused a 50-80% decrease in AUC in clinical evaluations. Examples of moderate inducers include, but are not limited to, bosentan, efavirenz, etravirine, modafinil, and nafcillin. Other examples of CPY3A inducers include, but are not limited to, phenobarbital, primidone, aminoglutethimide, phenytoin, oxcarbazepine, nevirapine, quercetin, capsaicin, bexarotene, dexamethasone, fosphenytoin, griseofulvin, rifabutin, and rifapentine.

In various aspects, the CYP3A4 inducer is a rifamycin antibiotic. Rifamycins are well characterized in the art, and have been proposed to act via inhibition of DNA-dependent RNA polymerase in bacteria. Examples of rifamycin antibiotics include, e.g., rifampin (also known as rifampicin), rifabutin, rifapentine, and rifaximin. In one aspect, the therapy comprises administering to a subject in need thereof a therapeutic amount of deflazacort and avoiding rifampin administration. In various aspects of the disclosure, the subject is in need of antibiotic therapy, such as a subject suffering from infection, e.g., a respiratory infection, which is a common complication of muscular dystrophy.

A "subject in need thereof" is a subject suffering from a disorder or condition responsive to deflazacort, such as DMD. In a particular aspect, the disorder or condition responsive to deflazacort is DMD. The subject is optionally 18 years or less in age. In various aspects, the subject also is in need of treatment with a CYP3A4 inducer or inhibitor. The term "therapeutically effective amount" refers to an amount of deflazacort sufficient to treat, ameliorate, or prevent an identified disease or condition that is responsive to deflazacort, or to exhibit a detectable therapeutic, prophylactic, or inhibitory effect on symptoms. For example, in patients suffering from DMD, a therapeutic effective amount is that which delays the onset of proximal muscle weakness of the legs and pelvis, loss of muscle mass, or fibrosis, or maintains the subject's ability to sit, stand independently, and walk. In various aspects, the therapeutically effective amount is determined using a combination of one or more factors selected from subject age, weight, ambulatory status and the presence or absence of an inducer or inhibitor of cytochrome P450 3A (e.g., CYP3A4).

An exemplary dose range based on age may be selected from 6-36, 30-72 or 36-72 mg/day; having alternative dose ranges selected from 6-12, 6-30, 12-24, 18-24, 20-36, 24-36, 30-36, 30-48, 30-54, 36-54, 36-60, 36-72, 42-60, 42-66, 42-72, 48-54, 48-72, 54-60, 54-66 or 54-72 mg/day; and, having target doses selected from 18, 24, 36, 42, 48, 54, 60 or 66 mg/day; or, an ambulatory dose range based on age may be selected from 6-18, 30-60 or 36-72 mg/day; having alternative dose ranges selected from 6-12, 12-18, 30-36, 30-48, 30-54, 36-54, 36-60, 42-60, 42-66, 42-72, 48-54, 48-72, 54-60, 54-66 or 54-72 mg/day; and, having target doses selected from 18, 36 or 42 mg/day; or, a nonambulatory dose range based on age may be selected from 12-30, 30-54 or 48-96 mg/day; having an alternative dose range selected from 12-18, 12-24, 18-24, 18-30, 30-36, 30-42, 36-54, 42-54, 48-54, 48-60, 48-72, 54-60, 54-72 or 54-96 mg/day; and, having target doses selected from 18, 24, 36, 42, 54 or 66 mg/day.

An exemplary dose range based on weight may be selected from 6-18, 6-36, 18-36, 24-66, 24-96 or 42-96 mg/day; having alternative dose ranges selected from 6-12, 6-18, 6-30, 12-18, 12-24, 18-24, 18-30, 18-36, 24-30, 24-36, 24-48, 24-54, 24-72, 30-42, 36-48, 36-54, 36-60, 36-66, 36-72, 36-96, 42-54, 42-60, 42-66, 42-72, 48-54, 48-66, 48-72, 48-96, 54-60, 54-66, 54-72 or 54-96 mg/day; and, having target doses selected from 12, 18, 24, 30, 36, 42, 48, 54 or 60 mg/day; or, an ambulatory dose range based on weight may be selected from 6-18, 12-36, 18-30, 24-60, 24-54 or 48-72 mg/day; having alternative dose ranges selected from 6-12, 12-18, 12-24, 12-30, 18-24, 18-30, 18-36, 24-30, 24-36, 24-48, 24-54, 30-42, 36-48, 36-54, 36-60, 36-66, 42-54, 42-60, 48-54, 48-60, 48-66, 54-60, 54-66 or 54-72 mg/day; and, having target doses selected from 12, 18, 24, 36, 48 or 54 mg/day; or, a non-ambulatory dose range based on weight may be selected from 12-24, 18-54, 24-36, 30-66, 30-72, or 54-96 mg/day; having alternative dose ranges selected from 12-18, 18-24, 18-30, 18-36, 24-30, 24-36, 24-48, 24-54, 30-36, 30-42, 30-48, 30-54, 30-60, 36-48, 36-54, 36-60, 36-72, 42-54, 42-60, 42-66, 48-54, 48-66, 54-66, 54-90, 60-90, 66-84, or 72-96 mg/day; and, having target doses selected from 18, 24, 30, 42, 54 or 66 mg/day.

In alternative aspects, the therapeutically effective amount is any of the fixed dosages described herein. It will be appreciated that the instant disclosure provides a therapy for treating DMD in an appropriate subject by administering a corresponding fixed dose referenced herein, as appropriate for any particular aspect. Use of deflazacort in a method of treatment (e.g., a method of treating DMD), and use of any of the dosages of deflazacort referenced herein in the preparation of a medicament also is provided.

In various aspects of the disclosure, the therapy comprises avoiding administration of CYP3A inducer (such as a CYP3A4 inducer, e.g., rifampin) or a CYP3A inhibitor (such as a CYP3A4 inhibitor). "Avoiding" is used in accordance with its customary meaning to mean, e.g., "refraining from." In some aspects, the therapy comprises discontinuing administration of the CYP3A inducer throughout the entire course of treatment with deflazacort. For example, the CYP3A inducer (e.g., rifampin) is discontinued at the time that administration of deflazacort begins. In other aspects, the CYP3A inducer is discontinued within at least three days to 1 month prior to or after starting deflazacort therapy. Avoiding co-administration of deflazacort and the CYP3A inducer (i.e., avoiding administration of the two agents within 24 hours of each other) also is contemplated. When the administration regimen includes a dosing reprieve (e.g., ten days of deflazacort treatment followed by ten days of no deflazacort administration), the CYP3A4 inducer is optionally administered during the period of reprieve.

The deflazacort therapy administered to a subject in need thereof can be improved by, for example, advising the subject that co-administration of deflazacort with a CYP3A4 inducer can alter the therapeutic effect of deflazacort. In some aspects, the subject is advised that a CYP3A4 inducer, such as a CYP3A4 inducer (e.g., rifampin) should be avoided or discontinued. Avoiding a CYP3A4 inducer, e.g., avoids reduced (decreased) exposure to the active metabolite of deflazacort, 21-desDFZ, or the potential for reduced exposure to 21-desDFZ.

The disclosure also provides a deflazacort therapy comprising, administering to a subject in need thereof a therapeutically effective amount of deflazacort and avoiding administration of an inhibitor of CYP3A, such as CYP3A4. For CYP enzymes, the FDA generally defines a "strong inhibitor" as one that causes a >5-Fold increase in the plasma AUC values or more than 80% decrease in clearance of CYP substrates (not limited to sensitive CYP substrate) in clinical evaluations. The FDA generally defines a "moderate inhibitor" as one that causes a >2-Fold but <5-Fold increase in the AUC values or 50-80% decrease in clearance of sensitive CYP substrates when the inhibitor is given at the highest approved dose and the shortest dosing interval in clinical evaluations. Examples of strong CYP3A inhibitors identified by the FDA include, for example, boceprevir, clarithromycin, conivaptan, indinavir, itraconazole, ketoconazole, lopinavir/ritonavir, mibefradil, nefazodone, nelfinavir, posaconazole, ritonavir, saquinavir, telaprevir, telithromycin, and voriconazole. Examples of moderate CYP3A inhibitors identified by the FDA include, for example, amprenavir, aprepitant, atazanavir, ciprofloxacin, darunavir/ritonavir, diltiazem, erythromycin, fluconazole, fosamprenavir, imatinib, and verapamil.

In various aspects of the disclosure, the therapy comprises discontinuing administration of a CYP3A4 inducer or inhibitor prior to starting deflazacort therapy. In some aspects, the CYP3A4 inducer or inhibitor is discontinued within one month prior to starting deflazacort therapy, within three weeks, within two weeks, or within one week prior to starting deflazacort therapy, or at the same time as starting deflazacort therapy. In other aspects, the CYP3A4 inducer or inhibitor is discontinued in response to starting deflazacort therapy and is discontinued within one week after starting deflazacort therapy.

In one aspect, the selection of factors used to determine the effective fixed target dose to be administered includes the presence or absence of an inducer or inhibitor of cytochrome P450 3A (CYP3A), in particular, concomitant administration of a CYP3A4 inducer, concomitant administration of a CYP3A4 inhibitor or concomitant administration of a P-glycoprotein (Pgp) inhibitor.

In another aspect, the CYP3A4 inducer is a moderate or strong CYP3A4 inducer.

In another aspect, the CYP3A4 inducer is a moderate CYP3A4 inducer and the dosage of deflazacort is increased about Two-Fold to about Three-Fold.

In another aspect, the CYP3A4 inducer is a strong CYP3A4 inducer and the dosage of deflazacort is increased about Four-Fold to about Six-Fold.

In another aspect, the CYP3A4 inhibitor is a moderate or strong CYP3A4 inhibitor.

In another aspect, the CYP3A4 inhibitor is a moderate CYP3A4 inhibitor and the dosage of deflazacort is reduced about Two-Fold to about Three-Fold.

In another aspect, the CYP3A4 inhibitor is a strong CYP3A4 inhibitor and the dosage of deflazacort is reduced about Three-Fold to about Four-Fold.

In another aspect, the fixed dose of deflazacort is reduced about Three-Fold to about Four-Fold during concomitant administration of a Pgp inhibitor.

Dosage Modifications

The disclosure further provides an improved deflazacort therapy involving dose modifications based on other factors not generally considered until applied in the therapy described herein. Previously, clinicians generally did not consider ambulatory status when determining deflazacort dosage in DMD patients; dosage was selected only based on weight to achieve a daily mg/kg dose. When ambulatory status was considered, clinicians generally reduced the dose of deflazacort or cycled the patient off the drug. Contrary to previous regimens, the present disclosure provides a deflazacort therapy to a subject suffering from DMD comprising, increasing the dosage administered to the subject when the subject loses ambulation. The terms "loses ambulation" or "becomes non-ambulatory" refer to the loss of the ability to walk, i.e., the subject requires a wheel chair. Loss of ambulation status has been defined a number of ways, but generally its definition includes, but is not limited to: the inability to walk independently or without support, a shifting of Grade 1 to Grade 0 on the North Star Ambulatory Assessment, the ability to perform the 6 minute walk test, among others. In various aspects, the dosage is increased by about 6 mg to about 12 mg per day (e.g., 6 mg or 12 mg per day) for subjects 18 years and under, and up to 24 mg (e.g., 6-24 mg) in subjects greater than 18 years of age. In various aspects, the therapy comprises increasing the dosage in the subject at risk of losing ambulation by 1.2 fold or 1.4 fold.

For example, in various aspects, when the subject is 30 kg or less and is ambulatory, the fixed dose is 12-36 mg per day (e.g., 12-24 mg per day, or 18 mg per day), whereas if the subject is non-ambulatory, and the fixed dose is 18-54 mg per day (e.g., 18-36 mg per day, 24-54 mg per day, or 24 mg per day). For various aspects of the therapy wherein the subject is greater than 30 kg, the fixed dose of deflazacort for an ambulatory subject is 24-60 mg per day (e.g., 36 mg per day), whereas the fixed dose for a non-ambulatory subject is 30-72 mg per day (e.g., 42 mg per day). For subjects greater than 30 kg and less than or equal to 50 kg, the fixed dose of deflazacort is optionally 24-54 mg per day (e.g., 24-48 mg per day, or 36 mg per day) for an ambulatory subject, whereas it is optionally 30-66 mg per day (e.g., 42 mg per day) for a non-ambulatory subject. In various aspects wherein the subject is greater than 50 kg, the fixed dose of deflazacort is optionally 48-72 mg per day (e.g., 54 mg per day or 60 mg per day) if ambulatory; if the subject is non-ambulatory, the fixed dose of deflazacort is 54-96 mg per day (e.g., 66 mg per day).

In various aspects, the deflazacort therapy administered to a subject in need thereof (e.g., a subject suffering from DMD) comprises, increasing the dosage of deflazacort administered to the subject during concomitant administration of a CYP3A inducer (e.g., a CYP3A4 inducer). Put another way, optionally, when a treatment regimen comprises administration of both deflazacort and a CYP3A inducer, the subject is administered a therapeutically effective amount of the CYP3A inducer and a dosage of deflazacort that is increased relative to the dose taken in the absence of the CYP3A4 inducer. In various aspects, the therapy comprises, increasing the dosage of deflazacort (e.g., any of the fixed doses set forth herein) about Two-Fold to about Six-Fold during concomitant administration of a CYP3A4 inducer (e.g., a CYP3A4 inducer such as, but not limited to, rifampin). For example, in one aspect, the dose of deflazacort is increased about Two-Fold to about Three-Fold during concomitant administration of a moderate CYP3A inducer. Alternatively, the therapy comprises increasing the dosage of deflazacort about Four-Fold to about Six-Fold during concomitant administration of a strong CYP3A inducer. To illustrate, in one aspect, a subject suffering from DMD is being treated with the strong CYP3A inducer rifampin, the therapy disclosed herein comprises, increasing the SOC weight-based dose of deflazacort (0.9 mg/kg) to about 3.2-6.4 mg/kg.

The disclosure further provides a deflazacort therapy administered to a subject in need thereof (e.g., a subject suffering from DMD) comprising, reducing the dosage of deflazacort administered to the subject during concomitant administration of a CYP3A inhibitor (e.g., CYP3A4 inhibitor). Put another way, optionally, when a treatment regimen comprises administration of both deflazacort and a CYP3A inhibitor, the subject is administered a therapeutically effective amount of the CYP3A4 inhibitor and a dosage of deflazacort that is reduced relative to the dose taken in the absence of the CYP3A4 inducer. In various embodiments, the therapy comprises reducing the dosage of deflazacort (e.g., any of the fixed doses set forth herein) about Two-Fold to about Three-Fold during concomitant administration with a CYP3A4 inhibitor. Alternatively, the therapy comprises reducing the dosage of deflazacort (e.g., any of the fixed doses set forth herein) about Three-Fold to about Four-Fold during concomitant administration with a CYP3A4 inhibitor. To illustrate, in one embodiment, a subject suffering from DMD is being treated with, e.g., clarithromycin, and the therapy comprises reducing the SOC weight-based dose of deflazacort (0.9 mg/kg) to about 0.3-0.45 mg/kg. Alternatively, for example, a 36 mg per day dose would be reduced to a 12 mg per day dose.

The disclosure further provides a deflazacort therapy to a subject in need thereof (e.g., a subject suffering from DMD) comprising, reducing the dosage of deflazacort administered to the subject during concomitant administration of a P-glycoprotein (Pgp) inhibitor. In various embodiments, concomitant use of moderate or strong Pgp inhibitors is avoided. If concomitant use of a moderate or strong Pgp inhibitor is not avoided, i.e., when a treatment regimen comprises administration of both deflazacort and a Pgp inhibitor, the subject is administered a therapeutically effective amount of the Pgp inhibitor and a dosage of deflazacort that is reduced relative to the dose taken in the absence of the Pgp inducer. In various embodiments, the therapy comprises reducing the dosage of deflazacort (e.g., any of the fixed doses set forth herein) about Two-Fold to about Three-Fold during concomitant administration with a Pgp inhibitor. Alternatively, the therapy comprises reducing the dosage of deflazacort (e.g., any of the fixed doses set forth herein) about Three-Fold to about Four-Fold during concomitant administration with a Pgp inhibitor. An inhibitor of Pgp is, for example, an agent that increases the area under the curve (AUC) of digoxin to ≥1.25-fold. Pgp inhibitors include, for example, Cyclosporine, Elacridar (GF120918), Ketoconazole, Quinidine, Reserpine, Ritonavir, Tacrolimus, Valspodar (PSC833), Verapamil, Zosuquidar (LY335979), amiodarone, carvedilol, clarithromycin, dronedarone, itraconazole, lapatinib, lopinavir, propafenone, quinidine, ranolazine, saquinavir, telaprevir, and tipranavir.

"Concomitant administration" is understood to be interchangeable with concurrent administration or co-administration. Thus, the term is understood to encompass administration of two agents simultaneously, or at different times, and by the same route or by different routes, as long as the agents are given in a manner that allows both agents to be affecting the body at the same time. In some embodiments, the subject is already being administered the CYP3A inducer or inhibitor or Pgp inhibitor. In other embodiments, the subject is already being administered deflazacort, CYP3A inhibitor or CYP3A inducer or Pgp inhibitor therapy is instituted, and the dose of deflazacort is adjusted as described herein. In related embodiments, the dosage of deflazacort is increased prior to administration of the CYP3A inducer, or decreased prior to administration of the CYP3A inhibitor or Pgp inhibitor.

The disclosure further provides a method of discontinuing deflazacort therapy, the method comprising reducing the daily dose of deflazacort administered to a subject undergoing deflazacort therapy by no greater than 6 mg every two weeks. Put another way, a subject administered a first daily dose of deflazacort is administered a second daily dose of deflazacort for a treatment period of two weeks, wherein the second daily dose is lower than the first daily dose, and the reduction in dosage between the first and second daily doses is no more than 6 mg. The subject optionally is administered a third daily dose for a second treatment period of two weeks, wherein the third daily dose is lower than the second daily dose, and the reduction in dosage between the second and third daily doses is no more than 6 mg. The two week step-down is optionally performed until the dosage reaches 0 mg (i.e., treatment withdrawal is complete).

All publications, patents and patent applications cited in this specification are herein incorporated by reference as if each individual publication or patent application were specifically and individually indicated to be incorporated by reference.

REFERENCES

Astellas Pharma (2015). "MYRBETRIQ-mirabegron tablet, film coated, extended release Prescribing Information." From dailymed.nlm.nih.gov/dailymed/fda/fdaDrugXsl.cfm?setid=ba9e9e15-e666-4c56-9271-2e24739cfa2d&type=display. (Labeled dose was assessed in a Phase 2 study, referred to as Study 3 in the package insert).

Bello L, Gordish-Dressman H, Morgenroth L P, Henricson E K, Duong T, Hoffman E P, et al, and the CINRG Investigators. Prednisone/prednisolone and deflazacort regimens in the CINRG Duchenne Natural History Study. Neurology. 2015; 85(12):1048-55.

Bushby K, Finkel R, Birnkrant D J, Case L E, Clemens P R, Cripe L, et al. Diagnosis and management of Duchenne muscular dystroph, part 2: implementation of multidisciplinary care. Lancet Neurol. 2010; 9(2):177-89.

Ciafaloni E, Fox D J, Pandya S, Westfield C P, Puzhankara S, Romitti P A, et al. Delayed diagnosis in duchenne muscular dystrophy: data from the Muscular Dystrophy Surveillance, Tracking, and Research Network (MD STARnet). J Pediatr. 2009; 155(3):380-5.

Eagle M, Baudouin S V, Chandler C, Giddings D R, Bullock R, Bushby K. Survival in Duchenne muscular dystrophy: improvements in life expectancy since 1967 and the impact of home nocturnal ventilation. Neuromuscul Disord. 2002; 12(10):926-9.

Huang, S. M., Abernethy, D. R., Wang, Y., Zhao, P., and Zineh, I. (2013). "The utility of modeling and simulation in drug development and regulatory review." J Pharm Sci 102(9): 2912-2923.

Humbertclaude V, Hamroun D, Bezzou K, Bérard C, Boespflug-Tanguy O, Bommelaer C, et al. Motor and respiratory heterogeneity in Duchenne patients: implication for clinical trials. Eur J Paediatr Neurol. 2012; 16(2):149-60.

Koenig M, Hoffman E P, Bertelson C J, Monaco A P, Feener C, Kunkel L M. Complete cloning of the Duchenne muscular dystrophy (DMD) cDNA and preliminary genomic organization of the DMD gene in normal and affected individuals. Cell. 1987; 50(3):509-17.

Lee, J. Y., Garnett, C. E., Gobburu, J. V., Bhattaram, V. A., Brar, S., Earp, J. C., Jadhav, P. R., Krudys, K., Lesko, L. J., Li, F., Liu, J., Madabushi, R., Marathe, A., Mehrotra, N., Tornoe, C., Wang, Y., and Zhu, H. (2011). "Impact of pharmacometric analyses on new drug approval and labelling decisions: a review of 198 submissions between 2000 and 2008." Clin Pharmacokinet 50(10): 627-635.

Manzur A Y, Kuntzer T, Pike M, Swan A. Glucocorticoid corticosteroids for Duchenne muscular dystrophy. Cochrane Database Syst Rev. 2008; 23(1):CD003725.

Mendell J R, Shilling C, Leslie N D, Flanigan K M, al-Dahhak R, Gastier-Foster J, et al. Evidence-based path to newborn screening for Duchenne muscular dystrophy. Ann Neurol. 2012; 71(3):304-13.

Yu, J., Chung, S., Zadezensky, I., Hu, K., Darstein, C., Nedelman, J., and Mehrotra, N. (2016). "Utility of Exposure-Response Analysis in Regulatory Decision on the Selection of Starting Dose of Pasireotide for Cushing Disease." J Clin Pharmacol 56(8): 1035-1038.

What is claimed:

1. A method for treating a subject that is suffering from Duchenne muscular dystrophy (DMD) comprising,
   (a) administering a target dose of deflazacort from a fixed target dose range; and
   (b) administering a higher dose of deflazacort that is 1.2 fold to 1.4 fold higher than the target dose when the subject becomes non-ambulatory.

2. The method of claim 1, wherein the fixed target dose range for a subject less than or equal to 11 years of age is 6-18 mg per day when the subject is ambulatory; or, wherein the fixed target dose range of deflazacort for a subject greater than 18 years of age is 36-72 mg per day when the subject is ambulatory.

3. The method of claim 1, wherein the fixed target dose range for a subject weight range less than or equal to 30 kg is 12-36 mg per day when the subject is ambulatory; or, wherein the fixed target dose range of deflazacort for a subject weight range greater than 50 kg is 48-72 mg per day when the subject is ambulatory.

4. The method of claim 1, wherein the target dose for a subject less than or equal to 11 years of age and having a subject weight range less than or equal to 30 kg is 18 mg per day when the subject is ambulatory, and the dose administered is 24 mg per day when the subject is non-ambulatory; or, wherein the target dose for a subject greater than 18 years of age and having a subject weight range greater than 50 kg is 48 mg per day when the subject is ambulatory, and the dose administered is 54 mg per day when the subject is non-ambulatory.

5. The method of claim 1, wherein the subject is administered a moderate CYP3A4 inducer and the dosage of deflazacort is increased about Two-Fold to about Three-Fold.

6. The method of claim 1, wherein the subject is administered a strong CYP3A4 inducer and the dosage of deflazacort is increased about Four-Fold to about Six-Fold.

7. The method of claim 1, wherein the subject is administered a moderate CYP3A4 inhibitor and the dosage of deflazacort is reduced about Two-Fold to about Three-Fold.

8. The method of claim 1, wherein the subject is administered a strong CYP3A4 inhibitor and the dosage of deflazacort is reduced about Three-Fold to about Four-Fold.

9. The method of claim 1, wherein the subject is administered a Pgp inhibitor and the fixed dose of deflazacort is reduced about Three-Fold to about Four-Fold.

10. The method of claim 1, wherein the fixed target dose range for a subject greater than 11 years of age and less than or equal to 18 years of age is 30-60 mg per day when the subject is ambulatory.

11. The method of claim 1, wherein for a subject with a weight range of greater than 30 kg and less than or equal to 50 kg the fixed target dose range is 24-60 mg per day when the subject is ambulatory.

12. The method of claim 1, wherein the higher dose is about 6 mg to about 24 mg more than the target dose.

13. The method of claim 12, wherein the target dose for a subject greater than 11 years of age and less than or equal to 18 years of age and having a subject weight range greater than 30 kg and less than or equal to 50 kg is 36 mg per day when the subject is ambulatory and the dose administered is 42 mg when the subject is non-ambulatory.

* * * * *